(12) United States Patent
Javaid et al.

(10) Patent No.: US 7,666,870 B2
(45) Date of Patent: *Feb. 23, 2010

(54) PHTHALAZINONE DERIVATIVES

(75) Inventors: Muhammad Hashim Javaid, Cambridge (GB); Graeme Cameron Murray Smith, Cambridge (GB); Niall Morrison Barr Martin, Cambridge (GB); Sylvie Gomez, Cambridge (GB); Vincent Junior Ming-Iai Loh, Cambridge (GB); Xiao-Ling Fan Cockcroft, Cambridge (GB); Stefano Forte, Cambridge (GB); Keith Allan Menear, Cambridge (GB); Ian Timothy William Matthews, Cambridge (GB); Frank Kerrigan, Tintagel (GB)

(73) Assignee: Maybridge Limited, Cornwall (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/143,208

(22) Filed: Jun. 20, 2008
(Under 37 CFR 1.47)

(65) Prior Publication Data
US 2009/0163477 A1  Jun. 25, 2009

Related U.S. Application Data

(63) Continuation of application No. 11/213,504, filed on Aug. 26, 2005, now Pat. No. 7,407,957.

(60) Provisional application No. 60/604,956, filed on Aug. 27, 2004.

(30) Foreign Application Priority Data
Aug. 26, 2004 (GB) ................ 0419072.4

(51) Int. Cl.
C07D 403/02 (2006.01)
A61K 31/502 (2006.01)
(52) U.S. Cl. ............ 514/248; 544/235; 544/237
(58) Field of Classification Search ......... 544/235, 544/237; 514/248
See application file for complete search history.

(56) References Cited

U.S. PATENT DOCUMENTS

| 3,813,384 | A | 5/1974 | Vogelsang et al. |
| 4,665,181 | A | 5/1987 | Thomas et al. |
| 4,841,047 | A | 6/1989 | Engel et al. |
| 5,032,617 | A | 7/1991 | Lee et al. |
| 5,041,653 | A | 8/1991 | Lee et al. |
| 5,215,738 | A | 6/1993 | Lee et al. |
| 5,556,856 | A | 9/1996 | Engel et al. |

(Continued)

FOREIGN PATENT DOCUMENTS

| DE | 2143745 | 3/1973 |
| DE | 3813531 | 4/1988 |
| DE | 287 032 | 2/1991 |

(Continued)

OTHER PUBLICATIONS

Vippagunta et al, "Crystalline Solids" Advanced Drug Delivery Reviews, vol. 48, pp. 3-26 (2001).*

(Continued)

*Primary Examiner*—Kahsay T Habte
(74) *Attorney, Agent, or Firm*—Michael Best & Friedrich LLP

(57) ABSTRACT

A compound of formula (I):

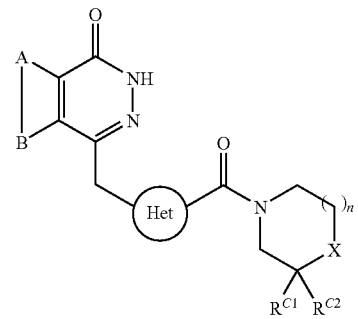

for use in treating cancer or other diseases ameliorated by the inhibition of PARP, wherein: A and B together represent an optionally substituted, fused aromatic ring; X can be $NR^X$ or $CR^X R^Y$; if $X=NR^X$ then n is 1 or 2 and if $X=CR^X R^Y$ then n is 1; $R^X$ is selected from the group consisting of H, optionally substituted $C_{1-20}$ alkyl, $C_{5-20}$ aryl, $C_{3-20}$ heterocyclyl, amido, thioamido, ester, acyl, and sulfonyl groups; $R^Y$ is selected from H, hydroxy, amino; or $R^X$ and $R^Y$ may together form a spiro-$C_{3-7}$ cycloalkyl or heterocyclyl group; $R^{C1}$ and $R^{C2}$ are independently selected from the group consisting of hydrogen and $C_{1-4}$ alkyl, or when X is $CR^X R^Y$, $R^{C1}$, $R^{C1}$, $R^{C2}$, $R^X$ and $R^Y$, together with the carbon atoms to which they are attached, may form an optionally substituted fused aromatic ring; $R^1$ is selected from H and halo; and Het is selected from:

(i)

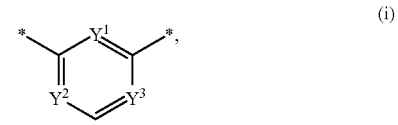

where $Y^1$ is selected from CH and N, $Y^2$ is selected from CH and N, $Y^3$ is selected from CH, CF and N, where only one or two of $Y^1$, $Y^2$ and $Y^3$ can be N; and (ii)

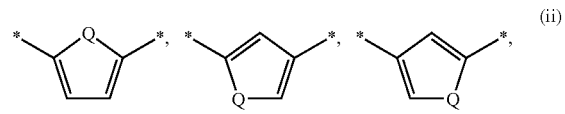

where Q is O or S.

5 Claims, No Drawings

U.S. PATENT DOCUMENTS

| | | | |
|---|---|---|---|
| 5,587,384 A | 12/1996 | Zhang et al. |
| 5,648,355 A | 7/1997 | Theoharides |
| 5,817,674 A | 10/1998 | Clemence et al. |
| 5,854,264 A | 12/1998 | Anthony et al. |
| 5,854,265 A | 12/1998 | Anthony |
| 5,859,035 A | 1/1999 | Anthony et al. |
| 5,872,136 A | 2/1999 | Anthony et al. |
| 5,874,444 A | 2/1999 | West |
| 5,874,452 A | 2/1999 | Anthony |
| 5,880,128 A | 3/1999 | Doll et al. |
| 5,880,140 A | 3/1999 | Anthony |
| 5,883,105 A | 3/1999 | Anthony |
| 5,886,178 A | 3/1999 | Allen et al. |
| 5,939,557 A | 8/1999 | Anthony et al. |
| 6,004,979 A | 12/1999 | Clemence et al. |
| 6,011,035 A | 1/2000 | Snutch et al. |
| 6,051,574 A | 4/2000 | Anthony |
| 6,060,038 A | 5/2000 | Burns et al. |
| 6,063,930 A | 5/2000 | Dinsmore et al. |
| 6,080,870 A | 6/2000 | Anthony et al. |
| 6,197,785 B1 | 3/2001 | Jackson et al. |
| 6,294,533 B1 | 9/2001 | Snutch et al. |
| 6,310,059 B1 | 10/2001 | Snutch |
| 6,340,684 B1 | 1/2002 | Napoletano et al. |
| 6,387,897 B1 | 5/2002 | Snutch |
| 6,426,415 B1 | 7/2002 | Jackson et al. |
| 6,465,467 B1 | 10/2002 | Nilsson et al. |
| 6,476,048 B1 | 11/2002 | Szabo et al. |
| 6,492,375 B2 | 12/2002 | Snutch |
| 6,498,160 B2 | 12/2002 | Napoletano et al. |
| 6,514,983 B1 | 2/2003 | Li |
| 6,514,984 B1 | 2/2003 | Watanabe |
| 6,552,016 B1 | 4/2003 | Ling et al. |
| 6,617,322 B2 | 9/2003 | Snutch |
| 6,635,642 B1 | 10/2003 | Jackson et al. |
| 6,677,333 B1 | 1/2004 | Seko et al. |
| 6,891,041 B2 | 5/2005 | Petrov et al. |
| 6,943,168 B2 | 9/2005 | Snutch et al. |
| 6,949,554 B2 | 9/2005 | Snutch et al. |
| 6,951,862 B2 | 10/2005 | Snutch et al. |
| 6,953,857 B2 | 10/2005 | Will et al. |
| 7,064,128 B2 | 6/2006 | Snutch et al. |
| 7,067,665 B2 | 6/2006 | Nazare et al. |
| 7,071,180 B2 | 7/2006 | Nilsson et al. |
| 7,151,102 B2 | 12/2006 | Martin et al. |
| 7,186,726 B2 | 3/2007 | Snutch et al. |
| 7,196,085 B2 | 3/2007 | Martin et al. |
| 7,407,957 B2 * | 8/2008 | Javaid et al. ............... 514/248 |
| 2001/0029258 A1 | 10/2001 | Snutch |
| 2003/0022819 A1 | 1/2003 | Ling et al. |
| 2003/0045530 A1 | 3/2003 | Snutch |
| 2003/0092694 A1 | 5/2003 | Nilsson et al. |
| 2003/0195192 A1 | 10/2003 | Haviv et al. |
| 2003/0195195 A1 | 10/2003 | Haviv et al. |
| 2004/0014744 A1 | 1/2004 | Haviv et al. |
| 2004/0023949 A1 | 2/2004 | Baxter et al. |
| 2004/0034035 A1 | 2/2004 | Snutch et al. |
| 2004/0044004 A1 | 3/2004 | Snutch et al. |
| 2004/0147529 A1 | 7/2004 | Snutch et al. |
| 2004/0192703 A1 | 9/2004 | Snutch et al. |
| 2004/0209872 A1 | 10/2004 | Snutch et al. |
| 2004/0242554 A1 | 12/2004 | Nilsson et al. |
| 2004/0259866 A1 | 12/2004 | Snutch et al. |
| 2004/0266784 A1 | 12/2004 | Snutch et al. |
| 2005/0020583 A1 | 1/2005 | Pulici |
| 2005/0054568 A1 | 3/2005 | Ling et al. |
| 2005/0059663 A1 | 3/2005 | Martin et al. |
| 2005/0080096 A1 | 4/2005 | Ishida et al. |
| 2005/0227919 A1 | 10/2005 | Ashworth et al. |
| 2005/0227999 A1 | 10/2005 | Pajouhesh et al. |
| 2005/0277629 A1 | 12/2005 | Lansbury et al. |
| 2006/0030557 A1 | 2/2006 | Haviv et al. |
| 2006/0063767 A1 | 3/2006 | Javaid et al. |
| 2006/0084660 A1 | 4/2006 | Snutch et al. |
| 2006/0142293 A1 | 6/2006 | Martin et al. |
| 2006/0276391 A1 | 12/2006 | Auricchio et al. |
| 2007/0093489 A1 | 4/2007 | Javaid et al. |
| 2007/0185105 A1 | 8/2007 | Snutch et al. |
| 2008/0146575 A1 | 6/2008 | Menear et al. |
| 2008/0255128 A1 | 10/2008 | Javaid et al. |

FOREIGN PATENT DOCUMENTS

| | | |
|---|---|---|
| EP | 0030861 | 6/1981 |
| EP | 0269968 | 6/1988 |
| EP | 0355750 | 2/1990 |
| EP | 0389995 | 10/1990 |
| EP | 0502575 | 9/1992 |
| EP | 0590551 | 4/1994 |
| EP | 0634404 | 1/1995 |
| EP | 0699754 | 3/1996 |
| EP | 0705903 | 4/1996 |
| EP | 0792643 | 9/1997 |
| EP | 1477175 | 11/2004 |
| EP | 1760071 | 3/2007 |
| FR | 2262513 | 9/1975 |
| GB | 721286 | 1/1955 |
| GB | 2384776 | 3/2004 |
| IT | MI98A001671 | 4/1999 |
| JP | 54156526 | 12/1979 |
| JP | 58164577 | 9/1983 |
| JP | 62-252774 | 11/1987 |
| WO | WO 91/18591 | 12/1991 |
| WO | WO 93/14086 | 7/1993 |
| WO | WO 94/10151 | 5/1994 |
| WO | WO 95/24379 | 9/1995 |
| WO | WO 96/19225 | 6/1996 |
| WO | WO 96/31501 | 10/1996 |
| WO | WO 97/36587 | 10/1997 |
| WO | WO 97/38664 | 10/1997 |
| WO | WO 97/45412 | 12/1997 |
| WO | WO 98/43477 | 10/1998 |
| WO | WO 98/51308 | 11/1998 |
| WO | WO 99/08680 | 2/1999 |
| WO | WO 99/11624 | 3/1999 |
| WO | WO 99/11645 | 3/1999 |
| WO | WO 99/11649 | 3/1999 |
| WO | WO 99/44612 | 9/1999 |
| WO | WO 99/47494 | 9/1999 |
| WO | WO 00/05219 | 2/2000 |
| WO | WO 00/42040 | 7/2000 |
| WO | WO 00/44726 | 8/2000 |
| WO | WO 00/67734 | 11/2000 |
| WO | 01/10856 | 2/2001 |
| WO | WO 01/12199 | 2/2001 |
| WO | WO 01/16136 | 3/2001 |
| WO | WO 01/16137 | 3/2001 |
| WO | WO 01/21615 | 3/2001 |
| WO | WO 01/23390 | 4/2001 |
| WO | WO 01/57038 | 8/2001 |
| WO | WO 01/79184 | 10/2001 |
| WO | WO 01/85686 | 11/2001 |
| WO | WO 01/85687 | 11/2001 |
| WO | WO 01/87845 | 11/2001 |
| WO | WO 01/90077 | 11/2001 |
| WO | WO 02/36576 | 5/2002 |
| WO | WO 02/44157 | 6/2002 |
| WO | WO 02/068407 | 9/2002 |
| WO | WO 02/090334 | 11/2002 |
| WO | WO 02/094790 | 11/2002 |
| WO | WO 03/007959 | 1/2003 |
| WO | WO 03/051879 | 6/2003 |
| WO | WO 03/055865 | 7/2003 |
| WO | WO 03/057145 | 7/2003 |

| | | |
|---|---|---|
| WO | WO 03/063874 | 8/2003 |
| WO | WO 03/070707 | 8/2003 |
| WO | WO 03/070726 | 8/2003 |
| WO | WO 03/080581 | 10/2003 |
| WO | WO 03/093261 | 11/2003 |
| WO | WO 2004/080976 | 9/2004 |
| WO | WO 2005/053662 | 6/2005 |
| WO | WO 2006/097176 | 9/2006 |
| WO | 2008/083027 | 7/2008 |

OTHER PUBLICATIONS

Gavezzotti, "Are Crystal Structures Predictable?" Accounts of Chemical Research, vol. 27, pp. 309-314 (1994).*

West, Anthony R., Solid State Chemistry and its Applications, Wiley, New York, 1988, pp. 358 & 365.*

Braga et al., "Making crystals from crystals: a green route to crystal engineering and polymorphism" ChemComm 2005, 3635-3645.*

Wolff Manfred E. "Burger's Medicinal Chemistry, 5ed, Part 1" John Wiley & Sons, 1995, pp. 975-977.*

Banker, G.S. et al, "Modern Pharmaceutics, 3ed." Marcel Dekker, New York, 1996, pp. 451 and 596.*

Iino, M. et al., "Rational design and evaluation of new lead compound structures for selective .beta.ARK1 inhibitors," J. Med. Chem. (2002) 45(11):2150-2159.

Menear, K.A. et al., "4-[3-(4-Cyclopropanecarbonylpiperazine-1-carbonyl)-4-fluorobenzyl]-2H-phthalazin-1-one: a novel bioavailable inhibitor of poly(ADP-ribose) polymerase-1," J. Med. Chem. (Published on Web. Sep. 19, 2008) 11 pages (A-K).

Affar, E. B. et al., "Immunodot blot method for the detection of poly(ADP-ribose) synthesized in vitro and in vivo," Anal. Biochem (1998) 259(2):280-283.

Al-Dabbagh and Smith, "Species differences in oxidative drug metabolism: some basic considerations." Archives of toxicology, Supplement. Archiv fur Toxikologie. Supplement, vol. 7, 219-231 (1984).

Ame, J-C. et al., "PARP-2, a novel mammalian DNA damage-dependent poly(ADP-ribose) polymerase," J. Biol. Chem. (1999) 274(25):17860-17868.

Ame, J-C. et al., "The PARP superfamily," BioEssays (2004) 26:882-893.

Angell, S.M. et al., "Consistent gene silencing in transgenic plants expressing a replicating potato virus X RNA," EMBO J. (1997) 16(12):3675-3684.

Arnaudeau, C. et al., "DNA double-strand breaks associated with replication forks are predominantly repaired by homologous recombination involving an exchange mechanism in mammalian cells," J. Mol. Biol (2001) 307:1235-1245.

Banasik, M. et al., "Specific Inhbitors of Poly (ADP-Ribose) Synthetase and Mono (ADP-Ribosyl) transferse", J. Biol. Chem., 1992, vol. 267, 1569-1575.

Banasik, M. et al., "Inhibitors and activators of ADP-ribosylation reactions," Mol. Cell Biochem. (1994) 138:185-197.

Ben-Hur, E. et al., "Inhibitors of poly (ADP-ribose) synthesis enhance radiation response by differentially affecting repair of potentially lethal versus sublethal damage," Br. J. Cancer (1984) 49(VI):39-42.

Berge et al., 1977, "Pharmaceutically Acceptable Salts," J. Pharm. Sci., vol. 66, 1-19. Protective Groups in Organic Synthesis (T. Green and P. Wuts, Wiley, 1991).

Berger, N. A. et al., "Poly (ADP-ribose) in cellular response to DNA damage", Radiation Research, 1985, vol. 101, 4-14.

Bhattacharyya, A. et al., "The breast cancer susceptibility gene BRCA1 is required for subnuclear assembly of Rad51 and survival following treatment with the DNA cross-linking agent cisplatin," J. Biol. Chem. (2000) 275(31): 23899-23903.

Bold, G. et al., "New anilinophthalazines as potent and orally well absorbed inhibitors of the VEGF receptor tyrosine kinases useful as antagonists of tumor-driven angiogenesis," J. Med. Chem. (2000) 43:3200 (Abstract).

Bold, G. et al., "New anilinophthalazines as potent and orally well absorbed inhibitors of the FEBF receptor tyrosine kinases useful as antagonists of tumour-driven angiogenesis", J. Med. Chem., 2000, vol. 43, No. 12, 2310-2323.

Bowman et al., "Differential effects of the poly (ADP-ribose) polymerase (PARP) inhibitor NU 1025 on topoisomerase I and II inhibitor cytotoxicity in L1210 cells in vitro," British Journal of Cancer, vol. 84(1), 106-112 (2001).

Brummelkamp, T. R. et al., "A system for stable expression of short interfering RNAs in mammalian cells," Science (2002) 296:550-553.

Bundgaard, H., Design of Prodrugs, 1 (1985) Elsevier Science Publishers.

Burzio, L. et al., "Poly (adenosine diphosphoribose) synthase activity of isolated nuclei of normal and leukemic leukocytes (38930)", Proc. Soc. Exp. Bio. Med., 1975, vol. 149, 933-938.

Calabrese, C.R. et al., "Identification of potent nontoxic poly(ADP-ribose) polymerase-1 inhibitors: chemopotentiation and pharmacological studies," Clin. Can. Res. (2003) 9:2711-2718.

Caldecott, K.W., "DNA single-strand break repair and spinocerebellar ataxia," Cell (2003) 112:7-10.

Cantoni, O. et al., "Hydrogen peroxide insult in cultured mammalian cells: relationships between DNA single-strand breakage, poly (ADP-ribose) metabolism and cell killing", Biochim. Biophys. Acta, 1989, vol. 1014, 1-7.

Catteau, A. et al., "Methylation of the BRCA1 promoter region in sporadic breast and ovarian cancer: correlation with disease characteristics," Oncogene (1999) 18:1957-1965.

Chalmers, A.J. , "Poly(ADP-ribose) polymerase-1 and ionizing radiation: sensor, signaller and therapeutic target," Clin. Onc. (2004) 16:29-39.

Chappuis, P. O. et al., "Risk Assessment and Genetic Testing," Cancer Treat. Res., 2002, vol. 107, 29-59.

Chiarugi, A., "Poly(ADP-ribose) polymerase: killer or conspirator? The 'suicide hypothesis' revisted," Trends in Pharm. Sci. (2002) 23(3):122-129.

Cosi, C. et al., "Poly (ADP-ribose) polymerase: early involvement in glutamate-induced neurotoxicity in cultured cerebellar granule cells", J.Neurosci. Res., 1994, vol. 39, 38-46.

Cosi, C., "New inhibitors of poly(ADP-ribose) polymerase and their potential therapeutic targets," Expert Opin. Ther. Patents (2002) 12(7): 1047-1071.

Couzin, J., "The twists and turns in BRCA's path," Science (2003) 302:591-592.

Crooke, S.T., "Therapeutic applications of oligonucleotides," Ann. Rev. Pharmacol. Toxicol. (1992) 32:329-376.

D'Adda Di Fagagna, F. et al., "Functions of poly(ADP-ribose) polymerase in controlling telomere length and chromosomal stability", Nature Gen., 1999, vol. 23, No. 1, 76-80.

D'Amours, D. et al., "Poly(ADP-ribosy)ation reactions in the regulation of nuclear functions", Biochem. J., 1999, vol. 342, 249-268.

D'Amours, D. et al., "The MRE11 complex: at the crossroads of DNA repair and checkpoint signalling," Mol. Cell Biol. (2002) 3:317-327.

D'Andrea, A. D. et al., "The fanconi anaemia/BRCA pathway," Nat. Rev. Cancer (2003) 3:23-34.

Dantzer, F. et al., "Base excision repair is imparied in mammalian cells lacking poly(ADP-ribose) polymerase-1," Biochemistry (2000) 39:7559-7569.

Dantzer, F. et al., "Involvement of poly(ADP-ribose) polymerase in base excision repair," Biochimie (1999) 81:69-75.

Davies, A. A. et al., "Role of BRCA2 in control of the RAD51 recombination and DNA repair protein," Mol. Cell (2001) 7:273-282.

Dillon, K. J. et al., "A flashplate assay for the identification of PARP-1 inhibitors," J. Biomolecular Screening (2003) 8(3):347-352.

Durkacz, B. W. et al., "(ADP-ribose)$_n$ participates in DNA excision repair", Nature, 1980, vol. 283, No. 7, 593-596.

Dusemund, "Isochino [3,2-a]phthalazin-5,8-dione", Arch. Pharm., (Weinhein) 1982, pp. 925-930. (English Abstract).

Dusemund, J., "Einfache synthese von isochino[2,3-c][2,3]benzoxazepinon und -[2,3] benzodiazepinonen sowie ihrer vorstufen," Arch. Pharm. (1988) 321:41-44.

Egawa, C. et al., "Decreased expression of BRCA2 mRNA predicts favorable response to docetaxel in breast cancer," Int. J. Cancer (2001) 95:255-259.

Egawa, C. et al., "Quantitative analysis of estrogen receptor-α and -β messenger RNA expression in normal and malignant thyroid tissues by real-time polymerase chain reaction," Oncology (2001) 61:293-298.

Ehrlich, H.A. et al., "Recent advances in the polymerase chain reaction," *Science* (1991) 252:1643-1650.

Elbashir, S. M. et al., "Duplexes of 21-nucleotide RNAs mediate RNA interference in cultured mammalian cells," *Nature* (2001) 411:494-498.

El-Tamaty et al., Synthesis and biological activity of some 4-benzyl-1(2H)-phthalazinone derivatives, *Indian J. Chemistry*, v. 35B, 1067-1072 (1996).

El-Tamaty, E-S.H. et al., "Synthesis and biological activity of some 4-benzyl-1(2H)-phthalazinone derivatives," Chem. Abs. (1996) 125:23, 125:300924j.

Esteller, M. et al., "Promoter hypermethylation and BRCA1 inactivation in sporadic breast and ovarian tumors," *J. Natl. Cancer Inst.* (2000) 92(7):564-569.

Ferraris, D. et al., "Design and synthesis of poly ADP-ribose polymerase-1 inhibitors. 2. Biological evaluation of Aza-5[H]-phenanthridin-6-ones as potent, aqueous-soluble compounds for the treatment of ischemic injuries," J. Med. Chem. (2003) 46:3138-3151.

Fire, A. et al., "Potent and specific genetic interference by double-stranded RNA in *Caenorhabditis elegans*," *Nature* (1998) 391:806-811.

Foray, N. et al., "A subset of ATM- and ATR-dependent phosphorylation events requires the BRCA1 protein," *Embo J.* (2003) 22(11):2860-2871.

*From DNA damage and stress signalling to cell death*, 2000, Eds. De Murcia, G and Shall, S, Oxford University Press.

Fujisawa Pharmaceutical Co., "Preaparation of 2-carboxyalkyl-4-aralkylphthalazine derivatives as aldose reductase inhibitors and a process for preparing them," Chemical Abstracts 109:6531.

Fuska, J. et al., "New Cytotoxic and antitumor agents," *Chemical Abstracts*, 104:102050 (1985).

Gaken, J. A. et al., "Efficient retroviral infection of mammalian cells is blocked by inhibition of poly(ADP-ribose) polymerase activity", *J. Virology*, 1996, vol. 70, No. 6, 3992-4000.

Griffin, C.S. et al., "Mammalian recombination-repair genes XRCC2 and XRCC3 promote correct chromosome segregation," Nature Cell Biol. (2000) 2:757-761.

Griffin et al., "The role of inhibitors of poly (ADP-ribose) polymerase as resistance-modifying agents in cancer therapy," *Biochim* vol. 77, 408-422 (1995).

Grube, K. et al., "Direct stimulation of poly(ADP ribose) polymerase in permeabilized cells by double-stranded DNA oligomers," Anal. Biochem. (1991) 193:236-239.

Haber, J. E., "DNA recombination: the replication connection," *Trends Biochem. Sci.* (1999) 24:271-275.

Hall, I.H. et al., "Cytotoxicity of imides-N-alkyl semicarbazones, thiosemicarbazones, acetylhydrazones and related derivatives," *Anti-Cancer Drugs* (and abstract 122:204573), V.6, 147-153 (1995).

Halldorsson, H. et al., "Poly(ADP-ribose) polymerase activity in nucleotide permeable cells," FEBS Lett. (1978) 85(2):349-352.

*Handbook of Pharmaceutical Additives*, 2001, 2 Ed., Synapse Information Resources Inc., Endicott, New York, USA.

*Hawley's Condensed Chemical Dictionary*, 13th ed., Van Nostrand Reinhold eds. 716 and 825 (1997).

Herceg, Z. et al., "Functions of poly(ADP-ribose) polymerase (PARP) in DNA repair, genomic intergrity and cell death," Mut. Res. (2001) 477:97-110.

Hirai, K. et al., "Aberration of poly(adenosine diphosphate-ribose) metabolism in human colon adenomatous polyps and cancers", *Cancer Res.*, 1983, vol. 43, 3441-3446.

Hiramoto, T. et al., "Mutations of a novel human RAD54 homologue, RAD54B, in primary cancer," *Oncogene* (1999) 18:3422-3426.

Hoeijmakers, J. H.J., "Genome maintenance mechanisms for preventing cancer," *Nature* (2001) 411:366-374.

Hughes-Davies, L. et al., "EMSY links the BRCA2 pathway to sporadic breast and ovarian cancer," *Cell* (2003) 115:523-535.

Islam, A.M. et al., "Thioarylidenephthalides and related compounds: Part II. Reactions with amino compounds," Chemical Abstracts (1977) 87:67943.

Islam, A.M. et al., "4, 5, 6, 7-Tetraiodo-3-benzalphthalides and related compounds," (1981) Chemical Abstracts 95:187182.

Islam, A.M. et al., "Action of phosphorus pentasulfide on the products of interaction of p-sulfamoylphenylacetic acids with phthalic anhydride," (1981) Chemical Abstracts 95:62106.

Jackson, S.P., "Sensing and repairing DNA double-strand breaks," Carcinogenesis (2002) 23(5):687-696.

Janatova, M. et al., "Detection of the most frequent mutations in BRCA1 gene on polyacrylamide gels containing spreadex polymer NAB," *Neoplasma* (2003) 50(4):246-250.

Jancarkova, N., "Detection and incidence of mutations of BRCA1 gene in patients with cancer of the breast and ovary," *Ceska Gynekol.* (2003) 68(1):11-16.

Jasin, M., "Homologous repair of DNA damage and tumorigenesis: the BRCA connection," *Oncogene* (2002) 21(58): 8981-8993.

Jijon, H.B. et al., "Inhibition of poly(ADP-ribose) polymerase attenuates inflammation in a model of chronic colitis," Am. J. Physiol. Gastrointest. Liver Physiol. (2000) 279:G641-G651.

Johnson, R.D. et al., "Mammalian XRCC2 promotes the repair of DNA double-strand breaks by homologous recombination," Nature (1999) 401:397-399.

Kanaar, R. et al., "Molecular mechanisms of DNA double-strand break repair," Trends Cell Biol. (1998) 8:483-489.

Kashani-Sabet, M. et al., "Application of ribozymes to cancer gene therapy," *Cancer Gene Therapy* (1995) 2(3):213-223.

Kawamura, I. et al., "Ponalrestat, an aldose reductase inhibitor," *Chemical Abstract* 132:273943.

Kerr, P. et al., "New complexities for BRCA1 and BRCA2," *Curr. Biol.* (2001) 11:R668-676.

Kerrigan, F. et al. "Imide-substituted 4-benzyl-2H-phthalazin-1-ones: potent inhibitors of poly(ADP-ribose) polymerase-1 (PARP-1)," Poster at 12th SCI-RSC Medicinal Chemistry Symposium, Cambridge, 7-10 (2003).

Khanna, K. K. et al., "DNA double-strand breaks: signaling, repair and the cancer connection," *Nat. Genet.* (2001) 27(3):247-254.

Kraakman-Van Der Zwet, M. et al., "Brca2 (XRCC11) deficiency results in radioresistant DNA synthesis and a higher frequency of spontaneous deletions," *Mol. Cell Biol.* (2002) 22(2):669-679.

Kuperstein, G. et al., "A rapid fluorescent multiplexed-PCR analysis (FMPA) for founder mutations in the BRCA1 and BRCA2 genes," Clin. Genet. (2000) 57:213-220.

Kupper, J-H. et al., "Trans-dominant inhibition of poly(ADP-ribosyl)ation potentiates carcinogen-induced gene amplification in SV40-transformed Chinese hamster cells," Cancer Res. (1996) 56:2715-2717.

Lakhani, S. R. et al., "The pathology of familial breast cancer: predictive value of immunohistochemical markers estrogen receptor, progesterone receptor, HER-2, and p53 in patients with mutations in BRCA1 and BRCA2," *J. Clin. Oncol.* (2002) 20(9):2310-2318.

Le Rhun, Y. et al., "Cellular responses to DNA damage in the absence of poly(ADP-ribose)polymerase", *Biochem. Biophys. Res. Commun.*, 1998, vol. 245, 1-10.

Lemay, M. et al., "Detection of DNA damage and identification of UV-induced photoproducts using the cometassay kit," *Biotechniques* (1999) 27:846-851.

Liaudet, L. et al., "Protection against hemorrhagic shock in mice genetically deficient in poly(ADP-ribose)polymerase", *Proc. Natl. Acad. Sci. U.S.A.*, 2000, vol. 97, No. 3, 10203-10208.

Lindahl, T. et al, "Quality control by DNA repair," Science (1999) 286:1897-1905.

Lindahl, T. et al, "Post-translational modification of poly(ADP-ribose) polymerase induced by DNA strand breaks," TIBS (1995) 20:405-411.

Lundin, C. et al., "Different roles for nonhomologous end joining and homologous recombination following replication arrest in mammalian cells," Mol. Cell. Biol. (2002) 22(16):5869-5878.

Lundin, C. et al., "RAD51 is involved in repair of damage associated with DNA replication in mammalian cells," J. Mol. Biol. (2003) 328:521-535.

Magnusson, J. et al., "Inhibitor of poly(ADP-ribose)transferase potentiates the recombinogenic but not the mutagenic action of alkylating agents in somatic cells in vivo in drosophila melanogaster," Mutagenesis (1990) 5(5):511-514.

Martin, N. et al., "Phthalazinone derivatives as potent PARP-1 inhibitors", 13th Intl. Symposium on ADP-ribosylation, 2001, Abstract 107.

Martin, N. et al., "DNA repair inhibition and cancer therapy," *J. Photochem. and PhotoBiol. B: Biology* (2001) 63:162-170.

Matsuda, M. et al., "Mutations in the RAD54 recombination gene in primary cancers," *Oncogene*(1999) 18:3427-3430.

Mcnealy, T. et al., "Intrinsic presence of poly (ADP-ribose) is significantly increased in malignant prostate compared to benign prostate cell lines," Anticancer Res. (2003) 23:1473-1478.

Menissier De Murcia, J. et al., "Requirement of poly(ADP-ribose)polymerase in recovery from DNA damage in mice and cells", *Proc. Natl. Acad. Sci. U.S.A.*, 1997, vol. 94, 7303-7307.

Menissier De Murcia, J. et al., "Functional interaction between PARP-1 and PARP-2 in chromosome stability and embryonic development in mouse," EMBO J. (2003) 22(9):2255-2263.

Mercola, D. et al., "Antisense approaches to cancer gene therapy," *Cancer Gene Therapy* (1995) 2(1):47-59.

Miwa, M. et al., "Cell density-dependent increase in chromatin-associated ADP-ribosyltransferase activity in simian virus 40-transformed cells", *Arch. Biochem. Biophys.*, 1977, vol. 181, 313-321.

Morrison, C. et al., "Genetic interaction between PARP and DNA-PK in V(D)J recombination and tumorigenesis," Nature Genetics (1997) 17:479-482.

Moynahan, M. E. et al., "Brca1 controls homology-directed DNA repair," *Mol. Cell* (1999) 4:511-518.

Moynahan, M. E. et al., "BRCA2 is required for homology-directed repair or chromosomal breaks," *Mol. Cell* (2001) 7:263-272.

Mullis, K. et al., "Specific enzymatic amplification of DNA in vitro: the polymerase chain reaction," *Cold Spring Harbor Symp. Quant. Biol.* (1987) 51:263-273.

Nakamura, J. et al., "Quantitation of intracellular NAD(P)H can monitor an imbalance of DNA single strand break repair in base excision repair deficient cells in real time," Nuc. Acids Res. (2003) 31(17):e104 1-7.

Nathanson, K. L. et al., "Breast cancer genetics: what we know and what we need," *Nat. Med.* (2001) 7(5):552-556.

Neuhausen, S. L. et al., "Mutation testing of early-onset breast cancer genes BRCA1 and BRCA2," *Genet. Test* (1997) 1(2):75-83.

Noel, G. et al., "Poly(ADP-ribse) polymerase (PARP-1) is not involved in DNA double-strand break recovery," BMC Cell Biol. (2003) 4:7-17.

Pacher et al., "The Role of Poly(ADP-Ribose) Polymerase Activation in the Development of Myocardial and Endothelial Dysfunction in Diabetes," *Diabetes*, 51:514-521 (2002).

Perkins, E. et al., "Novel inhibitors of poly(ADP-ribose)polymerase/PARP1 and PARP2 identified using a cell-based screen in yeast", *Cancer Res.*, vol. 61, 4175-4183 (2001).

Pierce, A.J. et al., "XRCC3 promotes homology-directed repair of DNA damage in mammalian cells," Genes & Dev. (1999) 13:2633-2638.

Radice, P. J., "Mutations of BRCA genes in hereditary breast and ovarian cancer," *Exp. Clin. Cancer Res.* (2002) 21(3 Suppl.):9-12.

Rattan, S. I. et al., "Kinetin delays the onset of ageing characteristics in human fibroblasts", *Biochem. Biophys. Res. Commun.*, 1994, vol. 201, No. 2, 665-672.

Said, S. I. et al., "Excitotoxicity in the lung: N-methy-D-aspartate-induced, nitric oxide-dependent, pulmonary edema is attenuated by vasoactive intestinal peptide and by inhibitors of poly(ADP-ribose)polymerase", *Proc. Natl. Acad. Sci. U.S.A.*, 1996, vol. 93, 4688-4692.

Samper, E. et al., "Normal telomere length and chromosomal end capping in poly(ADP-ribose) polymerase-deficient mice and primary cells despite increased chromosomal instability," J. Cell Biol. (2001) 154(1):49-60.

Satoh, M.S. et al., "Role of poly(ADP-ribose) formation in DNA repair," Nature (1992) 356:356-358.

Schlicker, A. et al., "4-Amino-1,8-napthalimide: a novel inhibitor of poly(ADP-ribose)polymerase and radiation sensitizer", *Int. J. Radiat. Bio.*, 1999, vol. 75, No. 1, 91-100.

Schreiber, V. et al., "A dominant-negative mutant of human poly(ADP-ribose) polymerase affects cell recovery, apoptosis, and sister chromatid exchange following DNA damage," Proc. Natl. Acad. Sci. USA (1995) 92:4753-4757.

Schreiber, V. et al., "Poly(ADP-ribose) polymerase-2 (PARP-2) is required for efficient base excision DNA repair in association with PARP-1 and XRCC1," J. Biol. Chem. (2002) 277(25):23028-23036.

Schultz, N. et al., "Poly(ADP-ribose) polymerase (PARP1) has a controlling role in homologous recombination," *Nucleic Acids Res.* (2003) 31:4959-4964.

Semionov, A. et al., "Inhibition of poly(ADP-ribose)polymerase stimulates extrachromosomal homologous recombination in mouse Ltk-fibroblasts," Nuc. Acids Res. (1999) 27(22):4526-4531.

Shah, G.M. et al., "Complete inhibition of poly(ADP-ribose) polymerase activity prevents the recovery of C3H10T1/2 cells from oxidative stress," Biochimica et Biophysica Acta (1996) 1312:1-7.

Shall, S. et al., "Poly(ADP-ribose) polymerase-1: what have we learned from the deficient mouse model?" *Mutat Res.* (2000) 460:1-15.

Shimizu, T. et al., "Inhibitory effects of azelastine and tranilast on leukotriene $B_4$ and leukotriene $C_4$ generation by rat colonic mucosa", *Prostaglandins Leukotrienes and Essential Fatty Acids*, 1995, vol. 53, 355-358.

Silverman, R.B., *The Organic Chemistry of Drug Design and Drug Action*, 352-400 (1992) Academic Press, Inc.

Simbulan-Rosenthal, C.M. et al., "Chromosomal aberrations in PARP-/-mice: genome stabilization in immortalized cells by reintroduction of poly(ADP-ribose) polymerase cDNA," Proc. Natl. Acad. Sci. USA (1999) 96(23):13191-13196.

Skehan, P. et al., "New colorimetric cytotoxicity assay for anticancer-drug screening", *J. Natl. Cancer Inst.*, 1990, vol. 82, No. 13, 1107-1112.

Southan, G.J. and Szabo, C., "Poly (ADP-ribose) polymerase inhibitors," *Current Medicinal Chemistry*, 10:4, 321-340 (2003).

Suto, M.J. et al., "Dihydroisoquinolinones: the design and synthesis of a new series of potent inhibitors of poly(ADP-ribose) polymerase," *Anticancer Drug Des.* (1991) 7:107-117.

Szabo, C. et al., "Endothelial dysfunction in a rat model of endotoxic shock", *J. Clin. Invest.*, 1997, vol. 100, 723-25.

Szabo, "PARP as a Therapeutic Target," Zhang, Ed. CRC Press (2002) 169-204.

Taniguchi, T. et al., "Disruption of the Fanconi anemia-BRCA pathway in cisplatin-sensitive ovarian tumors," *Nat. Med.* (2003) 9(5):568-574.

Tarsounas, M. et al., "BRCA2-dependent and independent formation of RAD51 nuclear foci," *Oncogene* (2003) 22:1115-1123.

Tebbs, R.S. et al., "Correction of chromosomal instability and sensitivity to diverse mutagens by a cloned cDNA of the XRCC3 DNA repair gene," Proc. Natl. Acad. Sci. USA (1995) 92:6354-6358.

Tentori, L. et al., "Potential clinical applications of poly(ADP-ribose) polymerase (PARP) inhibitors," Pharm. Res. (2002) 45(2):73-85.

Thompson, L. H. et al., "Recombinational DNA repair and human disease," *Mutat. Res.* (2002) 509:49-78.

Tracey, W. et al., "Aldose reductase inhibition alone or combined with an adenosine A3 agonist reduces ischemic myocardial injury," *Chemical Abstract* (2000) 134:65983.

Tutt, A. et al., "The relationship between the roles of BRCA genes in DNA repair and cancer predisposition," Trends Mol. Med. (2002) 8(12):571-576.

Tutt, A. et al., "Mutation in Brca2 stimulates error-prone homology-directed repair of DNA double-strand breaks occurring between repeated sequences," EMBO J. (2001) 20(17):4704-4716.

Tutt, A N.J. et al., "Disruption of Brca2 increases the spontaneous mutation rate in vivo: synergism with ionizing radiation," Embo Reports (2002) 3(3):255-260.

Uhlmann, E. et al., Antisense oligonucleotides: a new therapeutic principle, *Chem. Rev.* (1990) 90(4):543-584.

Van Gent, D.C. et al., "Chromosomal stability and the DNA double-stranded break connection," Nature Reviews (2001) 2:196-206.

Venkitaraman, A. R., "Cancer susceptibility and the functions of BRCA1 and BRCA2," Cell (2002) 108:171-182.

Virag and Szabo, "The Therapeutic Potential of Poly(ADP-Ribose) Polymerase Inhibitors," *Pharmacological Reviews*, vol. 54(3), (2002) 375-429.

Voinnet, O. et al. "Systemic signalling in gene silencing," *Nature* (1997) 389:553.

Waldman, A.S. et al., "Stimulation of intrachromosomal homologous recombination in mammalian cells by an inhibitor of poly(ADP-ribosylation)," Nuc. Acids Res. (1991) 19(21):5943-5947.

Wang, Z.-Q. et al., "Mice lacking ADPRT and poly(ADP-ribosyl)ation develop normally but are susceptible to skin disease", *Genes Dev.*, 1995, vol. 9, 509-520.

Wang, Z.-Q. et al., "PARP is important for genomic stability but dispensable in apoptosis," *Genes Dev.* (1997) 11:2347-2358.

West, A.R. "Solid State Chemistry and its Applications" Wiley, New York, 358 and 365 (1988).

Wood, R.D. et al., "Human DNA repair genes," *Science* (2001) 291:1284-1289.

Yamaguchi, M. et al., "Novel antiasthmatic agents with dual activities of thromboxane $A_2$ synthetase inhibition and bronchodilation. 1. 2-[2-(1-Imidazolyl)alkyl]-1(2*H*)-phthalazinones", *J. Med. Chem.*, 1993, vol. 36, No. 25, 4052-4060.

Yamaguchi, M. et al., "Novel antiasthmatic agents with dual activities of thromboxane $A_2$ synthetase inhibition and bronchodilation. 2. 4-(3-Pyridyl)-1(2*H*)-phthalazinones", *J. Med. Chem.*, 1993, vol. 36, No. 25, 4061-4068.

Zamore, P. D., "RNAi: double-stranded RNA directs the ATP-dependent cleavage of mRNA at 21 to 23 nucleotide intervals," *Cell* (2000) 101:25-33.

Zamore, P. D., "RNA interference: listening to the sound of silence," *Nature Structural Biology* (2001) 8(9):746-750.

Zhang, J. et al., "Neuroprotective effects of poly(ADP-ribose) polymerase inhibition on focal cerebral ischemia," Portland Press Proc. (1998) 15:125.

Zhong, Q. et al., "Association of BRCA1 with the hRad50-hMre11-p95 complex and the DNA damage response," *Science* (1999) 285:747-750.

Zingarelli, B. et al., "Activator protein-1 signalling pathway and apoptosis are modulated by poly(ADP-ribose) polymerase-1 in experimental colitis," Immunology (2004) 113:509-517.

Bloch, W. et al., "Poly-adenosine diphosphate-ribose polymerase inhibition for myocardial protection: pathophysiologic and physiologic considerations," J. Thoracic Card. Surg. (2004) 128(2):323-324.

Cockcroft, X-L. et al., "Phthalazinones 2: optimisation and synthesis of novel potent inhibitors of poly(ADP-ribose) polymerase," Biorg. Med. Chem. Lett. (2006) 16:1040-1044.

Cuzzocrea, S., "Shock, inflammation and PARP," Pharmacological Res. (2005) 52:72-82.

Greene, T.W. et al., Protective Groups in Organic Synthesis, Chapters 2 and 7, John Wiley & Sons Inc. (1999) p. 17-23 and 494-503.

Jantzen and Robinson, "B. Prodrugs," taken from Modern Pharmaceutics, Third Edition, Banker and Rhodes, editors (1996) p. 596.

Loh, V.M. et al., "Phthalazinones. Part 1: The design and synthesis of a novel series of potent inhibitors of poly(ADP-ribose)polymerase," Bioorg. Med. Chem. Lett. (2005) 15:2235-2238.

Miller, B.A., "Inhibition of TRPM2 function by PARP inhibitors protects cells from oxidative stress-induced death," Br. J. Pharmacology (2004) 143:515-516.

Szabo G. et al., "Poly-ADP-ribose polymerase inhibition protects against myocardial and endothelial reperfusion injury after hypothermic cardiac arrest," J. Thoracic Cardiovas. Surg. (2003) 126(3):651-658.

Tasatargil, A. et al., "Poly(ADP-ribose) polymerase inhibition prevents homocysteine-induced endothelial dysfunction in the isolated rat aorta," Pharmacology (2004) 72:99-105.

Vippagunta, S.R. et al., "Crystalline solids," Adv. Drug Delivery Reviews (2001) 48:3-26.

Gale, P.A. et al., "Calixpyrroles II," Coordination Chem. Rev. (2001) 222:57-102.

Zhang, W. et al., "Fluorous 2,4-dichloro-1,3,5-triazine (F-DCT) as amide coupling agent," QSAR Comb Sci. (2006) 25(8-9):724-727.

United States Office Action for U.S. Appl. No. 10/021,506 dated Nov. 26, 2003 (5 pages).

United States Office Action for U.S. Appl. No. 10/021,506 dated Sep. 7, 2004 (7 pages).

United States Office Action for U.S. Appl. No. 10/021,506 dated Jun. 15, 2005 (5 pages).

United States Office Action for U.S. Appl. No. 10/021,506 dated Nov. 21, 2005 (8 pages).

United States Office Action for U.S. Appl. No. 11/352,178 dated Nov. 7, 2008 (11 pages).

United States Office Action for U.S. Appl. No. 10/426,147 dated Oct. 28, 2004 (32 pages).

United States Office Action for U.S. Appl. No. 10/426,147 dated Aug. 9, 2005 (16 pages).

United States Office Action for U.S. Appl. No. 10/426,147 dated Apr. 25, 2006 (14 pages).

United States Office Action for U.S. Appl. No. 11/873,671 dated Sep. 3, 2008 (35 pages).

United States Office Action for U.S. Appl. No. 11/873,671 dated Mar. 6, 2009 (12 pages).

US 6,759,401, 07/2004, Nilsson et al. (withdrawn)

* cited by examiner

PHTHALAZINONE DERIVATIVES

This application is a continuation of U.S. patent application Ser. No. 11/213,504, filed Aug. 26, 2005, which claims the priority benefits of U.S. Provisional Patent Application No. 60/604,956, filed Aug. 27, 2004, and claims foreign priority benefits of GB0419072.4, filed Aug. 26, 2004, all of which are incorporated herein by reference.

The present invention relates to phthalazinone derivatives, and their use as pharmaceuticals. In particular, the present invention relates to the use of these compounds to inhibit the activity of the enzyme poly (ADP-ribose)polymerase-1, also known as poly(ADP-ribose)synthase and poly ADP-ribosyltransferase, and commonly referred to as PARP-1.

The mammalian enzyme PARP-1 (a 113-kDa multidomain protein) has been implicated in the signalling of DNA damage through its ability to recognize and rapidly bind to DNA single or double strand breaks (D'Amours, et al., *Biochem. J.*, 342, 249-268 (1999)).

The family of Poly (ADP-ribose) polymerases now includes around 18 proteins, that all display a certain level homology in their catalytic domain but differ in their cellular functions (Ame et al., *Bioessays.*, 26(8), 882-893 (2004)). Of this family PARP-1 (the founding member) and PARP-2 are so far the sole enzymes whose catalytic activity are stimulated by the occurrence of DNA strand breaks, making them unique in the family.

It is now known that PARP-1 participates in a variety of DNA-related functions including gene amplification, cell division, differentiation, apoptosis, DNA base excision repair as well as effects on telomere length and chromosome stability (d'Adda di Fagagna, et al., *Nature Gen.*, 23(1), 76-80 (1999)).

Studies on the mechanism by which PARP-1 modulates DNA repair and other processes has identified its importance in the formation of poly(ADP-ribose) chains within the cellular nucleus (Althaus, F. R. and Richter, C., ADP-Ribosylation of Proteins: Enzymology and Biological Significance, Springer-Verlag, Berlin (1987)). The DNA-bound, activated PARP-1 utilizes NAD$^+$ to synthesize poly (ADP-ribose) on a variety of nuclear target proteins, including topoisomerases, histones and PARP itself (Rhun, et al., *Biochem. Biophys. Res. Commun.*, 245, 1-10 (1998))

Poly (ADP-ribosyl)ation has also been associated with malignant transformation. For example, PARP-1 activity is higher in the isolated nuclei of SV40-transformed fibroblasts, while both leukemic cells and colon cancer cells show higher enzyme activity than the equivalent normal leukocytes and colon mucosa (Miwa, et al., *Arch. Biochem. Biophys.*, 181, 313-321 (1977); Burzio, et al., *Proc. Soc. Exp. Biol. Med.*, 149, 933-938 (1975); and Hirai, et al., *Cancer Res.*, 43, 3441-3446 (1983)). More recently in malignant prostate tumours compared to benign prostate cells significantly increased levels of active PARP (predominantly PARP-1) have been identified associated with higher levels of genetic instability (Mcnealy, et al., *Anticancer Res.*, 23, 1473-1478 (2003))

A number of low-molecular-weight inhibitors of PARP-1 have been used to elucidate the functional role of poly (ADP-ribosyl)ation in DNA repair. In cells treated with alkylating agents, the inhibition of PARP leads to a marked increase in DNA-strand breakage and cell killing (Durkacz, et al., *Nature*, 283, 593-596 (1980); Berger, N. A., *Radiation Research*, 101, 4-14 (1985)).

Subsequently, such inhibitors have been shown to enhance the effects of radiation response by suppressing the repair of potentially lethal damage (Ben-Hur, et al., *British Journal of Cancer*, 49 (Suppl. VI), 34-42 (1984); Schlicker, et al., *Int. J. Radiat. Bioi.*, 75, 91-100 (1999)). PARP inhibitors have been reported to be effective in radio sensitising hypoxic tumour cells (U.S. Pat. No. 5,032,617; U.S. Pat. No. 5,215,738 and U.S. Pat. No. 5,041,653). In certain tumour cell lines, chemical inhibition of PARP-1 (and PARP-2) activity is also associated with marked sensitisation to very low doses of radiation (Chalmers, *Clin. Oncol.*, 16(1), 29-39 (2004))

Furthermore, PARP-1 knockout (PARP −/−) animals exhibit genomic instability in response to alkylating agents and γ-irradiation (Wang, et al., *Genes Dev.*, 9, 509-520 (1995); Menissier de Murcia, et al., *Proc. Natl. Acad. Sci. USA*, 94, 7303-7307 (1997)). More recent data indicates that PARP-1 and PARP-2 possess both overlapping and non-redundant functions in the maintenance of genomic stability, making them both interesting targets (Menissier de Murcia, et al., *EMBO. J.*, 22(9), 2255-2263 (2003)).

A role for PARP-1 has also been demonstrated in certain vascular diseases, septic shock, ischaemic injury and neurotoxicity (Cantoni, et al., *Biochim. Biophys. Acta*, 1014, 1-7 (1989); Szabo, et al., *J. Clin. Invest.*, 100, 723-735 (1997)). Oxygen radical DNA damage that leads to strand breaks in DNA, which are subsequently recognised by PARP-1, is a major contributing factor to such disease states as shown by PARP-1 inhibitor studies (Cosi, et al., *J. Neurosci. Res.*, 39, 38-46 (1994); Said, et al., *Proc. Natl. Acad. Sci. U.S.A.*, 93, 4688-4692 (1996)). More recently, PARP has been demonstrated to play a role in the pathogenesis of haemorrhagic shock (Liaudet, et al., *Proc. Natl. Acad. Sci. U.S.A.*, 97(3), 10203-10208 (2000)).

It has also been demonstrated that efficient retroviral infection of mammalian cells is blocked by the inhibition of PARP-1 activity. Such inhibition of recombinant retroviral vector infections was shown to occur in various different cell types (Gaken, et al., *J. Virology*, 70(6), 3992-4000 (1996)). Inhibitors of PARP-1 have thus been developed for the use in anti-viral therapies and in cancer treatment (WO 91/18591).

Moreover, PARP-1 inhibition has been speculated to delay the onset of aging characteristics in human fibroblasts (Rattan and Clark, *Biochem. Biophys. Res. Comm.*, 201(2), 665-672 (1994)). This may be related to the role that PARP plays in controlling telomere function (d'Adda di Fagagna, et al., *Nature Gen.*, 23(1), 76-80 (1999)).

PARP-1 inhibitors are also thought to be relevant to the treatment of inflammatory bowel disease (Szabo C., Role of Poly(ADP-Ribose) Polymerase Activation in the Pathogenesis of Shock and Inflammation, In PARP as a Therapeutic Target; Ed J. Zhang, 2002 by CRC Press; 169-204), ulcerative colitis (Zingarelli, B, et al., *Immunology*, 113(4), 509-517 (2004)) and Crohn's disease (Jijon, H. B., et al., *Am. J. Physiol. Gastrointest. Liver Physiol.*, 279, G641-G651 (2000).

Some of the present inventors have previously described (WO 02/36576) a class of 1(2H)-phthalazinone compounds which act as PARP inhibitors. The compounds have the general formula:

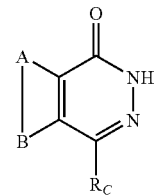

where A and B together represent an optionally substituted, fused aromatic ring and where $R_C$ is represented by -L-$R_L$. A large number of examples are of the formula:

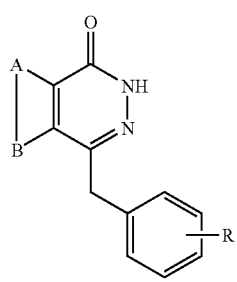

where R represent one or more optional substituents.

The present inventors have now discovered that compounds where R is of a certain nature and the phenyl group is replaced exhibit surprising levels of inhibition of the activity of PARP, and/or of potentiation of tumour cells to radiotherapy and various chemotherapies.

Accordingly, the first aspect of the present invention provides a compound of the formula (I):

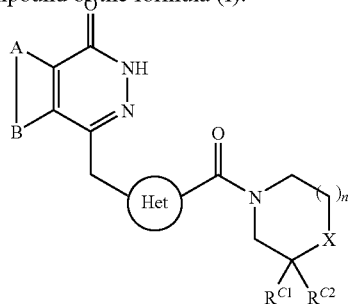

and isomers, salts, solvates, chemically protected forms, and prodrugs thereof wherein:

A and B together represent an optionally substituted, fused aromatic ring;

X can be $NR^X$ or $CR^XR^Y$;

if $X=NR^X$ then n is 1 or 2 and if $X=CR^XR^Y$ then n is 1;

$R^X$ is selected from the group consisting of H, optionally substituted $C_{1-20}$ alkyl, $C_{5-20}$ aryl, $C_{3-20}$ heterocyclyl, amido, thioamido, ester, acyl, and sulfonyl groups;

$R^Y$ is selected from H, hydroxy, amino;

or $R^X$ and $R^Y$ may together form a spiro-$C_{3-7}$ cycloalkyl or heterocyclyl group;

$R^{C1}$ and $R^{C2}$ are independently selected from the group consisting of hydrogen and $C_{1-4}$ alkyl, or when X is $CR^XR^Y$, $R^{C1}$, $R^{C2}$, $R^X$ and $R^Y$, together with the carbon atoms to which they are attached, may form an optionally substituted fused aromatic ring;

$R^1$ is selected from H and halo; and

Het is selected from:

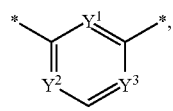

where $Y^1$ is selected from CH and N, $Y^2$ is selected from CH and N, $Y^3$ is selected from CH, CF and N, where only one or two of $Y^1$, $Y^2$ and $Y^3$ can be N; and

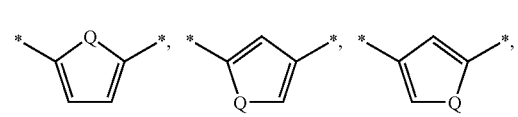

where Q is O or S.

Therefore, if X is $CR^XR^Y$, then n is 1 and the compound is of formula (Ia):

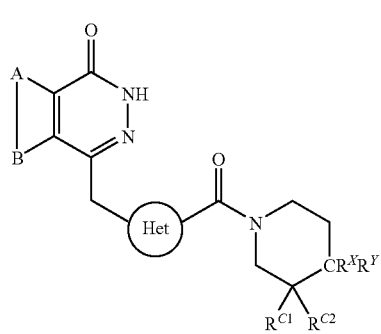

If X is $NR^X$, and n is 1, the compound is of formula (Ib):

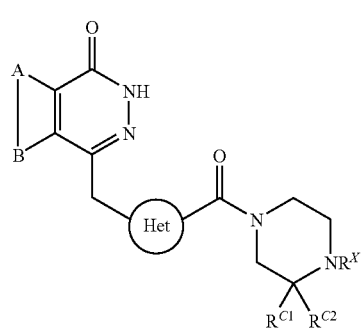

If X is $NR^X$, and n is 2, the compound is of formula (Ic):

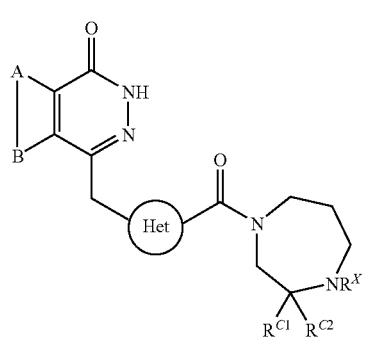

The possibilities for Het are:

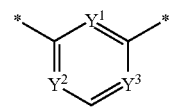

| Formula | | | |
|---|---|---|---|
| $Y^1$ | $Y^2$ | $Y^3$ | Group |
| N | CH | CH | |

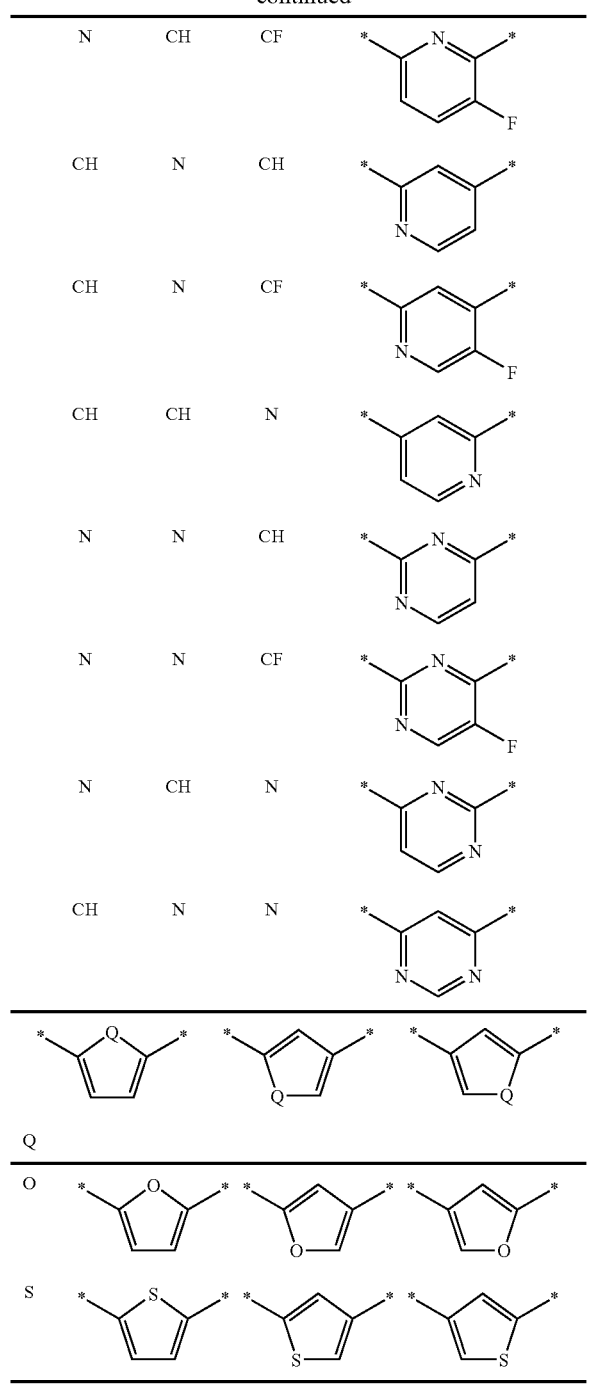

A second aspect of the present invention provides a pharmaceutical composition comprising a compound of the first aspect and a pharmaceutically acceptable carrier or diluent.

A third aspect of the present invention provides the use of a compound of the first aspect in a method of treatment of the human or animal body.

A fourth aspect of the present invention provides the use of a compound as defined in the first aspect of the invention in the preparation of a medicament for:

(a) preventing poly(ADP-ribose) chain formation by inhibiting the activity of cellular PARP (PARP-1 and/or PARP-2);

(b) the treatment of: vascular disease; septic shock; ischaemic injury, both cerebral and cardiovascular; reperfusion injury, both cerebral and cardiovascular; neurotoxicity, including acute and chronic treatments for stroke and Parkinsons disease; haemorraghic shock; inflammatory diseases, such as arthritis, inflammatory bowel disease, ulcerative colitis and Crohn's disease; multiple sclerosis; secondary effects of diabetes; as well as the acute treatment of cytoxicity following cardiovascular surgery or diseases ameliorated by the inhibition of the activity of PARP;

(c) use as an adjunct in cancer therapy or for potentiating tumour cells for treatment with ionizing radiation or chemotherapeutic agents.

In particular, compounds as defined in the first aspect of the invention can be used in anti-cancer combination therapies (or as adjuncts) along with alkylating agents, such as methyl methanesulfonate (MMS), temozolomide and dacarbazine (DTIC), also with topoisomerase-1 inhibitors like Topotecan, Irinotecan, Rubitecan, Exatecan, Lurtotecan, Gimetecan, Diflomotecan (homocamptothecins); as well as 7-substituted non-silatecans; the 7-silyl camptothecins, BNP 1350; and non-camptothecin topoisomerase-1 inhibitors such as indolocarbazoles also dual topoisomerase-I and II inhibitors like the benzophenazines, XR 11576/MLN 576 and benzopyridoindoles. Such combinations could be given, for example, as intravenous preparations or by oral administration as dependent on the preferred method of administration for the particular agent.

Other further aspects of the invention provide for the treatment of disease ameliorated by the inhibition of PARP, comprising administering to a subject in need of treatment a therapeutically-effective amount of a compound as defined in the first aspect, preferably in the form of a pharmaceutical composition and the treatment of cancer, comprising administering to a subject in need of treatment a therapeutically-effective amount of a compound as defined in the first aspect in combination, preferably in the form of a pharmaceutical composition, simultaneously or sequentially with radiotherapy (ionizing radiation) or chemotherapeutic agents.

In further aspects of the present invention, the compounds may be used in the preparation of a medicament for the treatment of cancer which is deficient in Homologous Recombination (HR) dependent DNA double strand break (DSB) repair activity, or in the treatment of a patient with a cancer which is deficient in HR dependent DNA DSB repair activity, comprising administering to said patient a therapeutically-effective amount of the compound.

The HR dependent DNA DSB repair pathway repairs double-strand breaks (DSBs) in DNA via homologous mechanisms to reform a continuous DNA helix (K. K. Khanna and S. P. Jackson, Nat. Genet. 27(3): 247-254 (2001)). The components of the HR dependent DNA DSB repair pathway include, but are not limited to, ATM (NM_000051), RAD51 (NM_002875), RAD51 L1 (NM_002877), RAD51C (NM_002876), RAD51 L3 (NM_002878), DMC1 (NM_007068), XRCC2 (NM_005431), XRCC3 (NM_005432), RAD52 (NM_002879), RAD54L (NM_003579), RAD54B (NM_012415), BRCA1 (NM_007295), BRCA2 (NM_000059), RAD50 (NM_005732), MRE11A (NM_005590) and NBS1 (NM_002485). Other proteins involved in the HR dependent DNA DSB repair pathway include regulatory factors such as EMSY (Hughes-Davies, et al., Cell, 115, pp 523-535). HR components are also described in Wood, et al., Science, 291, 1284-1289 (2001).

A cancer which is deficient in HR dependent DNA DSB repair may comprise or consist of one or more cancer cells which have a reduced or abrogated ability to repair DNA DSBs through that pathway, relative to normal cells i.e. the activity of the HR dependent DNA DSB repair pathway may be reduced or abolished in the one or more cancer cells.

The activity of one or more components of the HR dependent DNA DSB repair pathway may be abolished in the one or more cancer cells of an individual having a cancer which is deficient in HR dependent DNA DSB repair. Components of the HR dependent DNA DSB repair pathway are well characterised in the art (see for example, Wood, et al., *Science,* 291, 1284-1289 (2001)) and include the components listed above.

In some preferred embodiments, the cancer cells may have a BRCA1 and/or a BRCA2 deficient phenotype i.e. BRCA1 and/or BRCA2 activity is reduced or abolished in the cancer cells. Cancer cells with this phenotype may be deficient in BRCA1 and/or BRCA2, i.e. expression and/or activity of BRCA1 and/or BRCA2 may be reduced or abolished in the cancer cells, for example by means of mutation or polymorphism in the encoding nucleic acid, or by means of amplification, mutation or polymorphism in a gene encoding a regulatory factor, for example the EMSY gene which encodes a BRCA2 regulatory factor (Hughes-Davies, et al., *Cell,* 115, 523-535) or by an epigenetic mechanism such as gene promoter methylation.

BRCA1 and BRCA2 are known tumour suppressors whose wild-type alleles are frequently lost in tumours of heterozygous carriers (Jasin M., *Oncogene,* 21(58), 8981-93 (2002); Tutt, et al., *Trends Mol. Med.,* 8(12), 571-6, (2002)). The association of BRCA1 and/or BRCA2 mutations with breast cancer is well-characterised in the art (Radice, P. J., *Exp Clin Cancer Res.,* 21(3 Suppl), 9-12 (2002)). Amplification of the EMSY gene, which encodes a BRCA2 binding factor, is also known to be associated with breast and ovarian cancer.

Carriers of mutations in BRCA1 and/or BRCA2 are also at elevated risk of cancer of the ovary, prostate and pancreas.

In some preferred embodiments, the individual is heterozygous for one or more variations, such as mutations and polymorphisms, in BRCA1 and/or BRCA2 or a regulator thereof. The detection of variation in BRCA1 and BRCA2 is well-known in the art and is described, for example in EP 699 754, EP 705 903, Neuhausen, S. L. and Ostrander, E. A., *Genet. Test,* 1, 75-83 (1992); Janatova M., et al., *Neoplasma,* 50(4), 246-50 (2003). Determination of amplification of the BRCA2 binding factor EMSY is described in Hughes-Davies, et al., *Cell,* 115, 523-535).

Mutations and polymorphisms associated with cancer may be detected at the nucleic acid level by detecting the presence of a variant nucleic acid sequence or at the protein level by detecting the presence of a variant (i.e. a mutant or allelic variant) polypeptide.

DEFINITIONS

The term "aromatic ring" is used herein in the conventional sense to refer to a cyclic aromatic structure, that is, a cyclic structure having delocalised π-electron orbitals.

The aromatic ring fused to the main core, i.e. that formed by -A-B-, may bear further fused aromatic rings (resulting in, e.g. naphthyl or anthracenyl groups). The aromatic ring(s) may comprise solely carbon atoms, or may comprise carbon atoms and one or more heteroatoms, including but not limited to, nitrogen, oxygen, and sulfur atoms. The aromatic ring(s) preferably have five or six ring atoms.

The aromatic ring(s) may optionally be substituted. If a substituent itself comprises an aryl group, this aryl group is not considered to be a part of the aryl group to which it is attached. For example, the group biphenyl is considered herein to be a phenyl group (an aryl group comprising a single aromatic ring) substituted with a phenyl group. Similarly, the group benzylphenyl is considered to be a phenyl group (an aryl group comprising a single aromatic ring) substituted with a benzyl group.

In one group of preferred embodiments, the aromatic group comprises a single aromatic ring, which has five or six ring atoms, which ring atoms are selected from carbon, nitrogen, oxygen, and sulfur, and which ring is optionally substituted. Examples of these groups include, but are not limited to, benzene, pyrazine, pyrrole, thiazole, isoxazole, and oxazole. 2-Pyrone can also be considered to be an aromatic ring, but is less preferred.

If the aromatic ring has six atoms, then preferably at least four, or even five or all, of the ring atoms are carbon. The other ring atoms are selected from nitrogen, oxygen and sulphur, with nitrogen and oxygen being preferred. Suitable groups include a ring with: no hetero atoms (benzene); one nitrogen ring atom (pyridine); two nitrogen ring atoms (pyrazine, pyrimidine and pyridazine); one oxygen ring atom (pyrone); and one oxygen and one nitrogen ring atom (oxazine).

If the aromatic ring has five ring atoms, then preferably at least three of the ring atoms are carbon. The remaining ring atoms are selected from nitrogen, oxygen and sulphur. Suitable rings include a ring with: one nitrogen ring atom (pyrrole); two nitrogen ring atoms (imidazole, pyrazole); one oxygen ring atom (furan); one sulphur ring atom (thiophene); one nitrogen and one sulphur ring atom (isothiazole, thiazole); and one nitrogen and one oxygen ring atom (isoxazole or oxazole).

The aromatic ring may bear one or more substituent groups at any available ring position. These substituents are selected from halo, nitro, hydroxy, ether, thiol, thioether, amino, $C_{1-7}$ alkyl, $C_{3-20}$ heterocyclyl and $C_{5-20}$ aryl. The aromatic ring may also bear one or more substituent groups which together form a ring. In particular these may be of formula —(CH$_2$)$_m$— or —O—(CH$_2$)$_p$—O—, where m is 2, 3, 4 or 5 and p is 1, 2 or 3.

Alkyl: The term "alkyl" as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated or unsaturated (e.g. partially unsaturated, fully unsaturated). Thus, the term "alkyl" includes the sub-classes alkenyl, alkynyl, cycloalkyl, cycloalkyenyl, cylcoalkynyl, etc., discussed below.

In the context of alkyl groups, the prefixes (e.g. $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$ alkyl", as used herein, pertains to an alkyl group having from 1 to 4 carbon atoms. Examples of groups of alkyl groups include $C_{1-4}$ alkyl ("lower alkyl"), $C_{1-7}$ alkyl, and $C_{1-20}$ alkyl. Note that the first prefix may vary according to other limitations; for example, for unsaturated alkyl groups, the first prefix must be at least 2; for cyclic alkyl groups, the first prefix must be at least 3; etc.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include, but are not limited to, iso-propyl ($C_3$), iso-butyl ($C_4$), sec-butyl ($C_4$), tert-butyl ($C_4$), iso-pentyl ($C_5$), and neo-pentyl ($C_5$).

Alkenyl: The term "alkenyl", as used herein, pertains to an alkyl group having one or more carbon-carbon double bonds. Examples of alkenyl groups include $C_{2-4}$ alkenyl, $C_{2-7}$ alkenyl, $C_{2-20}$ alkenyl.

Examples of (unsubstituted) unsaturated alkenyl groups include, but are not limited to, ethenyl (vinyl, —CH═CH$_2$), 1-propenyl (—CH═CH—CH$_3$), 2-propenyl (allyl, —CH—CH═CH$_2$), isopropenyl (1-methylvinyl, —C(CH$_3$)═CH$_2$), butenyl ($C_4$), pentenyl ($C_5$), and hexenyl ($C_6$).

Alkynyl: The term "alkynyl", as used herein, pertains to an alkyl group having one or more carbon-carbon triple bonds. Examples of alkynyl groups include $C_{2-4}$ alkynyl, $C_{2-7}$ alkynyl, $C_{2-20}$ alkynyl.

Examples of (unsubstituted) unsaturated alkynyl groups include, but are not limited to, ethynyl (ethinyl, —C≡CH) and 2-propynyl (propargyl, —CH$_2$—C≡CH).

Cycloalkyl: The term "cycloalkyl", as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated (e.g. partially unsaturated, fully unsaturated), which moiety has from 3 to 20 carbon atoms (unless otherwise specified), including from 3 to 20 ring atoms. Thus, the term "cycloalkyl" includes the sub-classes cycloalkenyl and cycloalkynyl. Preferably, each ring has from 3 to 7 ring atoms. Examples of groups of cycloalkyl groups include $C_{3-20}$ cycloalkyl, $C_{3-15}$ cycloalkyl, $C_{3-10}$ cycloalkyl, $C_{3-7}$ cycloalkyl.

Examples of cycloalkyl groups include, but are not limited to, those derived from
saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_{10}$);
unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$), dimethylcyclohexene ($C_8$);
saturated polycyclic hydrocarbon compounds:
thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin (decahydronaphthalene) ($C_{10}$);
unsaturated polycyclic hydrocarbon compounds:
camphene ($C_{10}$), limonene ($C_{10}$), pinene ($C_{10}$);
polycyclic hydrocarbon compounds having an aromatic ring:
indene ($C_9$), indane (e.g., 2,3-dihydro-1H-indene) ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), aceanthrene ($C_{16}$), cholanthrene ($C_{20}$).

Heterocyclyl: The term "heterocyclyl", as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms. Examples of groups of heterocyclyl groups include $C_{3-20}$ heterocyclyl, $C_{5-20}$ heterocyclyl, $C_{3-15}$ heterocyclyl, $C_{5-15}$ heterocyclyl, $C_{3-12}$ heterocyclyl, $C_{5-12}$ heterocyclyl, $C_{3-10}$ heterocyclyl, $C_{5-10}$ heterocyclyl, $C_{3-7}$ heterocyclyl, $C_{5-7}$ heterocyclyl, and $C_{5-6}$ heterocyclyl.

Examples of monocyclic heterocyclyl groups include, but are not limited to, those derived from:
$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);
$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);
$S_1$: thiirane ($C_3$), thietane ($C_4$), thiolane (tetrahydrothiophene) ($C_5$), thiane (tetrahydrothiopyran) ($C_6$), thiepane ($C_7$);
$O_2$: dioxolane ($C_5$), dioxane ($C_6$), and dioxepane ($C_7$);
$O_3$: trioxane ($C_6$);
$N_2$: imidazolidine ($C_5$), pyrazolidine (diazolidine) ($C_5$), imidazoline ($C_5$), pyrazoline (dihydropyrazole) ($C_5$), piperazine ($C_6$);
$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);
$N_1S_1$: thiazoline ($C_5$), thiazolidine ($C_5$), thiomorpholine ($C_6$);
$N_2O_1$: oxadiazine ($C_6$);
$O_1S_1$: oxathiole ($C_5$) and oxathiane (thioxane) ($C_6$); and,
$N_1O_1S_1$: oxathiazine ($C_6$).

Examples of substituted (non-aromatic) monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Spiro-$C_{3-7}$ cycloalkyl or heterocyclyl: The term "spiro $C_{3-7}$ cycloalkyl or heterocyclyl" as used herein, refers to a $C_{3-7}$ cycloalkyl or $C_{3-7}$ heterocyclyl ring joined to another ring by a single atom common to both rings.

$C_{5-20}$ aryl: The term "$C_{5-20}$ aryl" as used herein, pertains to a monovalent moiety obtained by removing a hydrogen atom from an aromatic ring atom of a $C_{5-20}$ aromatic compound, said compound having one ring, or two or more rings (e.g., fused), and having from 5 to 20 ring atoms, and wherein at least one of said ring(s) is an aromatic ring. Preferably, each ring has from 5 to 7 ring atoms.

The ring atoms may be all carbon atoms, as in "carboaryl groups" in which case the group may conveniently be referred to as a "$C_{5-20}$ carboaryl" group.

Examples of $C_{5-20}$ aryl groups which do not have ring heteroatoms (i.e. $C_{5-20}$ carboaryl groups) include, but are not limited to, those derived from benzene (i.e. phenyl) ($C_6$), naphthalene ($C_{10}$), anthracene ($C_{14}$), phenanthrene ($C_{14}$), and pyrene ($C_{16}$).

Alternatively, the ring atoms may include one or more heteroatoms, including but not limited to oxygen, nitrogen, and sulfur, as in "heteroaryl groups". In this case, the group may conveniently be referred to as a "$C_{5-20}$ heteroaryl" group, wherein "$C_{5-20}$" denotes ring atoms, whether carbon atoms or heteroatoms. Preferably, each ring has from 5 to 7 ring atoms, of which from 0 to 4 are ring heteroatoms.

Examples of $C_{5-20}$ heteroaryl groups include, but are not limited to, $C_5$ heteroaryl groups derived from furan (oxole), thiophene (thiole), pyrrole (azole), imidazole (1,3-diazole), pyrazole (1,2-diazole), triazole, oxazole, isoxazole, thiazole, isothiazole, oxadiazole, tetrazole and oxatriazole; and $C_6$ heteroaryl groups derived from isoxazine, pyridine (azine), pyridazine (1,2-diazine), pyrimidine (1,3-diazine; e.g., cytosine, thymine, uracil), pyrazine (1,4-diazine) and triazine.

The heteroaryl group may be bonded via a carbon or hetero ring atom.

Examples of $C_{5-20}$ heteroaryl groups which comprise fused rings, include, but are not limited to, $C_9$ heteroaryl groups derived from benzofuran, isobenzofuran, benzothiophene, indole, isoindole; $C_{10}$ heteroaryl groups derived from quinoline, isoquinoline, benzodiazine, pyridopyridine; $C_{14}$ heteroaryl groups derived from acridine and xanthene.

The above alkyl, heterocyclyl, and aryl groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Nitro: —$NO_2$.

Cyano (nitrile, carbonitrile): —CN.

Acyl (keto): —C(=O)R, wherein R is an acyl substituent, for example, H, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), or a $C_{5-20}$ aryl group (also referred to as $C_{5-20}$ arylacyl), preferably a $C_{1-7}$ alkyl group. Examples of acyl groups include, but are not limited to, —C(=O)$CH_3$ (acetyl), —C(=O)$CH_2CH_3$ (propionyl), —C(=O)C$(CH_3)_3$ (butyryl), and —C(=O)Ph (benzoyl, phenone).

Carboxy (carboxylic acid): —COOH.

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)O$CH_3$, —C(=O)O$CH_2CH_3$, —C(=O)OC$(CH_3)_3$, and —C(=O)OPh.

Amido (carbamoyl, carbamyl, aminocarbonyl, carboxamide): —C(=O)$NR^1R^2$, wherein $R^1$ and $R^2$ are independently amino substituents, as defined for amino groups. Examples of amido groups include, but are not limited to, —C(=O)$NH_2$, —C(=O)NH$CH_3$, —C(=O)N$(CH_3)_2$, —C(=O)NH$CH_2CH_3$, and —C(=O)N$(CH_2CH_3)_2$, as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinylcarbonyl.

Amino: —$NR^1R^2$, wherein $R^1$ and $R^2$ are independently amino substituents, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, $R^1$ and $R^2$, taken together with the nitrogen atom to which they are attached, form a heterocyclic ring having from 4 to 8 ring atoms. Examples of amino groups include, but are not limited to, —$NH_2$, —NH$CH_3$, —NHCH$(CH_3)_2$, —N$(CH_3)_2$, —N$(CH_2CH_3)_2$, and —NHPh. Examples of cyclic amino groups include, but are not limited to, aziridinyl, azetidinyl, pyrrolidinyl, piperidino, piperazinyl, perhydrodiazepinyl, morpholino, and thiomorpholino. In particular, the cyclic amino groups may be substituted on their ring by any of the substituents defined here, for example carboxy, carboxylate and amido.

Acylamido (acylamino): —$NR^1$C(=O)$R^2$, wherein $R^1$ is an amide substituent, for example, hydrogen, a $C_{1-7}$ alkyl group, a $C_{3-20}$ heterocyclyl group, or a $C_{5-20}$ aryl group, preferably H or a $C_{1-7}$ alkyl group, most preferably H, and $R^2$ is an acyl substituent, for example, a $C_{1-7}$ alkyl group, a $C_{3-20}$ heterocyclyl group, or a $C_{5-20}$ aryl group, preferably a $C_{1-7}$ alkyl group. Examples of acylamide groups include, but are not limited to, —NHC(=O)$CH_3$, —NHC(=O)$CH_2CH_3$, and —NHC(=O)Ph. $R^1$ and $R^2$ may together form a cyclic structure, as in, for example, succinimidyl, maleimidyl, and phthalimidyl:

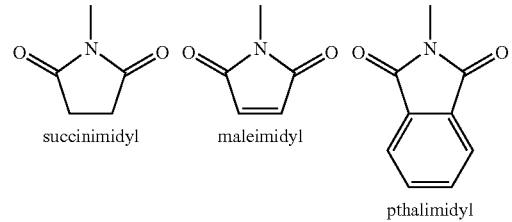

succinimidyl      maleimidyl      pthalimidyl

Ureido: —N($R^1$)CON$R^2R^3$ wherein $R^2$ and $R^3$ are independently amino substituents, as defined for amino groups, and $R^1$ is a ureido substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group. Examples of ureido groups include, but are not limited to, —NHCON$H_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, —NMeCONEt$_2$ and —NHCONHPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)$CH_3$ (acetoxy), —OC(=O)$CH_2CH_3$, —OC(=O)C$(CH_3)_3$, —OC(=O)Ph, —OC(=O)$C_6H_4$F, and —OC(=O)$CH_2$Ph.

Thiol: —SH.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —S$CH_3$ and —S$CH_2CH_3$.

Sulfoxide (sulfinyl): —S(=O)R, wherein R is a sulfoxide substituent, for example, a $C_{1-7}$ alkyl group, a $C_{3-20}$ heterocyclyl group, or a $C_{5-20}$ aryl group, preferably a $C_{1-7}$ alkyl group. Examples of sulfoxide groups include, but are not limited to, —S(=O)CH$_3$ and —S(=O)CH$_2$CH$_3$.

Sulfonyl (sulfone): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group. Examples of sulfone groups include, but are not limited to, —S(=O)$_2$CH$_3$ (methanesulfonyl, mesyl), —S(=O)$_2$CF$_3$, —S(=O)$_2$CH$_2$CH$_3$, and 4-methylphenylsulfonyl (tosyl).

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Sulfonamino: —NR$^1$S(=O)$_2$R, wherein R$^1$ is an amino substituent, as defined for amino groups, and R is a sulfonamino substituent, for example, a $C_{1-7}$alkyl group, a $C_{3-20}$heterocyclyl group, or a $C_{5-20}$aryl group, preferably a $C_{1-7}$alkyl group. Examples of sulfonamino groups include, but are not limited to, —NHS(=O)$_2$CH$_3$, —NHS(=O)$_2$Ph and —N(CH$_3$)S(=O)$_2$C$_6$H$_5$.

As mentioned above, the groups that form the above listed substituent groups, e.g. $C_{1-7}$ alkyl, $C_{3-20}$ heterocyclyl and $C_{5-20}$ aryl, may themselves be substituted. Thus, the above definitions cover substituent groups which are substituted.

Further Preferences

The following preferences can apply to each aspect of the present invention, where applicable.

In the present invention, the fused aromatic ring(s) represented by -A-B- preferably consist of solely carbon ring atoms, and thus may be benzene, naphthalene, and is more preferably benzene. As described above, these rings may be substituted, but in some embodiments are preferably unsubstituted.

If the fused aromatic ring represented by -A-B- bears a substituent group, it is preferably attached to the atom which itself is attached to the central ring β- to the carbon atom in the central ring. Thus, if the fused aromatic ring is a benzene ring, the preferred place of substitution is shown in the formula below by *:

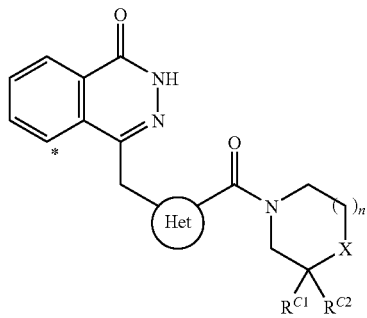

which is usually termed the 5-position of the phthalazinone moiety.

The substituent is preferably an alkoxy, amino, halo (e.g. fluoro) or hydroxy group, and more preferably a $C_{1-7}$ alkoxy group (e.g. —OMe).

If the substituent is a halo, it may be at the 8-position of the phthalazinone moiety.

Preferably, Het is selected from pyridylene, fluoropyrdiylene, furanylene and thiophenylene.

More preferably Het is selected from:

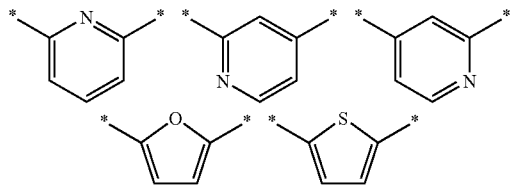

Most preferably Het is selected from:

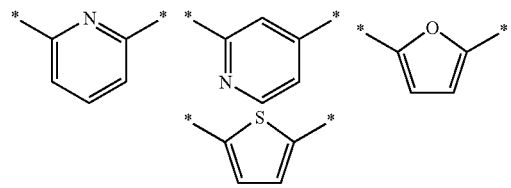

It is preferred that R$^{C1}$ and R$^{C2}$ are independently selected from hydrogen and $C_{1-4}$ alkyl, and more preferably H and methyl. It is more preferred that at least one of R$^{C1}$ and R$^{C2}$ are hydrogen, with the most preferred option being that both are hydrogen.

When n is 2, X is NR$^X$. In these embodiments, R$^X$ is preferably selected from the group consisting of: H; optionally substituted $C_{1-20}$ alkyl (for example, optionally substituted $C_{5-20}$ arylmethyl); optionally substituted $C_{5-20}$ aryl; optionally substituted ester groups, wherein the ester substituent is preferably $C_{1-20}$ alkyl; optionally substituted acyl groups; optionally substituted amido groups; optionally substituted thioamido groups; and optionally substituted sulfonyl groups. R$^X$ is more preferably selected from the group consisting of: H; optionally substituted $C_{1-20}$ alkyl (more preferably optionally substituted $C_{1-7}$ alkyl, e.g. methyl); and optionally substituted ester groups, wherein the ester substituent is preferably $C_{1-20}$ alkyl (more preferably optionally substituted $C_{1-7}$ alkyl, e.g. t-butyl).

When n is 1, X may be NR$^X$ or CR$^X$CR$^Y$.

In embodiments where X is NR$^X$, R$^X$ is preferably selected from the group consisting of: H; optionally substituted $C_{1-20}$ alkyl (for example, optionally substituted $C_{5-20}$ arylmethyl); optionally substituted $C_{5-20}$ aryl; optionally substituted acyl; optionally substituted sulfonyl; optionally substituted amido; and optionally substituted thioamido groups.

In these embodiments, it is preferred that Het is pyridylene.

When Het is pyridylene, R$^X$ is more preferably selected from the group consisting of: optionally substituted acyl; optionally substituted sulfonyl; and optionally substituted amido.

When Het is furanylene or thiophenylene, R$^X$ is more preferably selected from the group consisting of: optionally substituted $C_{1-20}$ alkyl (for example, optionally substituted $C_{5-20}$ arylmethyl); optionally substituted $C_{5-20}$ aryl; optionally substituted acyl; optionally substituted sulfonyl; and optionally substituted amido.

In embodiments where X is CR$^X$R$^Y$, R$^Y$ is preferably H. R$^X$ is preferably selected from the group consisting of: H; optionally substituted $C_{1-20}$ alkyl (for example, optionally substituted $C_{5-20}$ arylmethyl); optionally substituted $C_{5-20}$ aryl; optionally substituted $C_{3-20}$ heterocyclyl; optionally substituted acyl, wherein the acyl substituent is preferably selected from $C_{5-20}$ aryl and $C_{3-20}$ heterocylyl (e.g. piperazinyl); optionally substituted amino, wherein the amino groups are preferably selected from H and $C_{1-20}$ alkyl or together with the nitrogen atom, form a $C_{5-20}$ heterocyclic group; optionally substituted amido, wherein the amino groups are preferably selected from H and $C_{1-20}$ alkyl or together with the nitrogen atom, form a $C_{5-20}$ heterocyclic group; and optionally substituted ester groups, wherein the ester substituent is preferably selected from $C_{1-20}$ alkyl groups.

In these embodiments, when Het is furanylene or thiophenylene, $R^X$ is more preferably selected from optionally substituted amino, wherein the amino groups are preferably selected from H and $C_{1-20}$ alkyl or together with the nitrogen atom, form a $C_{5-20}$ heterocyclic group, e.g. morpholino.

Particularly preferred compounds include: 2, 3, 5, 6, 9, 10, 12, 13, 56, 57, 58, 62, 65, 66, 67, 74 and 75.

Where appropriate, the above preferences may be taken in combination with each other.

Includes Other Forms

Included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diasterioisomeric, epimeric, stereoisomeric, tautomeric, conformational, or anomeric forms, including but not limited to, cis- and trans-forms; E- and Z-forms; c-, t-, and r-forms; endo- and exo-forms; R—, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

If the compound is in crystalline form, it may exist in a number of different polymorphic forms.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hyroxyazo, and nitro/aci-nitro.

Particularly relevant to the present invention is the tautomeric pair illustrated below:

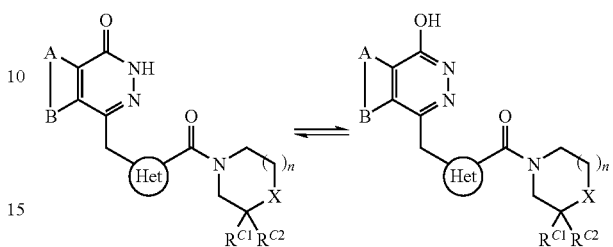

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below, as well as its different polymorphic forms.

It may be convenient or desirable to prepare, purify, and/or handle a corresponding salt of the active compound, for example, a pharmaceutically-acceptable salt. Examples of pharmaceutically acceptable salts are discussed in Berge, et al., "Pharmaceutically Acceptable Salts", *J. Pharm. Sci.*, 66, 1-19 (1977).

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous. Examples of suitable organic anions include, but are not limited to, those derived from the following organic acids: acetic, propionic, succinic, gycolic, stearic, palmitic, lactic, malic, pamoic, tartaric, citric, gluconic, ascorbic, maleic, hydroxymaleic, phenylacetic, glutamic, aspartic, benzoic, cinnamic, pyruvic, salicyclic, sulfanilic, 2-acetyoxybenzoic, fumaric, toluenesulfonic, methanesulfonic, ethanesulfonic, ethane disulfonic, oxalic, isethionic, valeric, and gluconic. Examples of suitable polymeric anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form," as used herein, pertains to a compound in which one or more reactive functional groups are protected from undesirable chemical reactions, that is, are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, "Protective Groups in Organic Synthesis" (T. Green and P. Wuts; 3rd Edition; John Wiley and Sons, 1999).

For example, a hydroxy group may be protected as an ether (—OR) or an ester (—OC(=O)R), for example, as: a t-butyl ether; a benzyl, benzhydryl (diphenylmethyl), or trityl (triphenylmethyl)ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide or a urethane, for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases, as an N-oxide (>NO.).

For example, a carboxylic acid group may be protected as an ester for example, as: a C$_{1-7}$ alkyl ester (e.g. a methyl ester; a t-butyl ester); a C$_{1-7}$ haloalkyl ester (e.g. a C$_{1-7}$ trihaloalkyl ester); a triC$_{1-7}$ alkylsilyl-C$_{1-7}$ alkyl ester; or a C$_{5-20}$ aryl-C$_{1-7}$ alkyl ester (e.g. a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties.

For example, some prodrugs are esters of the active compound (e.g. a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required. Examples of such metabolically labile esters include, but are not limited to, those wherein R is C$_{1-20}$ alkyl (e.g. -Me, -Et); C$_{1-7}$ aminoalkyl (e.g. aminoethyl; 2-(N,N-diethylamino)ethyl; 2-(4-morpholino)ethyl); and acyloxy-C$_{1-7}$ alkyl (e.g. acyloxymethyl; acyloxyethyl; e.g. pivaloyloxymethyl; acetoxymethyl; 1-acetoxyethyl; 1-(1-methoxy-1-methyl)ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy)carbonyloxymethyl; 1-(4-tetrahydropyranyloxy)carbonyloxyethyl; (4-tetrahydropyranyl)carbonyloxymethyl; and 1-(4-tetrahydropyranyl)carbonyloxyethyl).

Further suitable prodrug forms include phosphonate and glycolate salts. In particular, hydroxy groups (—OH), can be made into phosphonate prodrugs by reaction with chlorodibenzylphosphite, followed by hydrogenation, to form a phosphonate group —O—P(=O)(OH)$_2$. Such a group can be cleaved by phosphatase enzymes during metabolism to yield the active drug with the hydroxy group.

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Acronyms

For convenience, many chemical moieties are represented using well known abbreviations, including but not limited to, methyl (Me), ethyl (Et), n-propyl (nPr), iso-propyl (iPr), n-butyl (nBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et$_2$O), acetic acid (AcOH), dichloromethane (methylene chloride, DCM), trifluoroacetic acid (TFA), dimethylformamide (DMF), tetrahydrofuran (THF), and dimethylsulfoxide (DMSO).

Synthesis

In the synthesis routes given below, the A-B fused ring is shown as a fused benzene ring for convenience. Compounds in which the A-B ring is other than benzene may be synthesised using methodologies analogous to those described below by the use of appropriate alternative starting materials.

Compounds of the present invention may be synthesised by reaction of a compound of Formula 1:

Formula 1

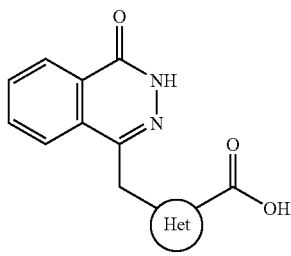

in which Het is as previously defined, with a compound of Formula 2:

Formula 2

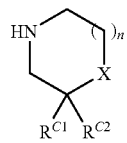

in which n, $R^{C1}$, $R^{C2}$ and X are as previously defined, in the presence of a coupling reagent system, for example 2-(1H-benzotriazol-1-yl)-1,1,3,3-tetramethyluronium tetrafluoroborate, 2-(1H-benzotriazol-1-yl)-1,1,3,3-tetramethyluronium hexafluorophosphate or (dimethylaminopropyl) ethylcarbodiimide hydrochloride/hydroxybenzotriazole, in the presence of a base, for example diisopropylethylamine, in a solvent, for example dimethylacetamide or dichloromethane, at a temperature in the range of 0° C. to the boiling point of the solvent used.

Alternatively, compounds of the present invention may be synthesised by conversion of a compound of Formula 1 into an activated species, for example an acid chloride or an activated ester such as an N-hydroxysuccinimide ester, using well-known methodologies, and reaction of the activated species with a compound of Formula 2.

Compounds of Formula 1 may be synthesised by reaction of a compound of Formula 3:

Formula 3

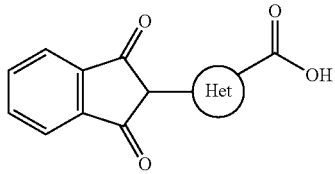

in which $R^1$ is as previously defined, or a compound of Formula 4:

Formula 4

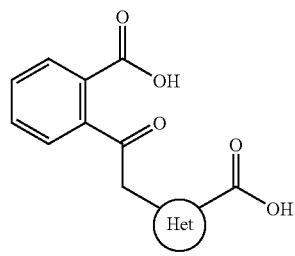

in which $R^1$ is as previously defined, or a mixture of a compound of Formula 3 and a compound of Formula 4, with a source of hydrazine, for example hydrazine hydrate or hydrazine monohydrate, optionally in the presence of a base, for example triethylamine, optionally in the presence of a solvent, for example industrial methylated spirit, at a temperature in the range of 0° C. to the boiling point of the solvent used.

Compounds of Formula 3 or Formula 4, or mixtures thereof, may be synthesised by reaction of a compound of Formula 5:

Formula 5

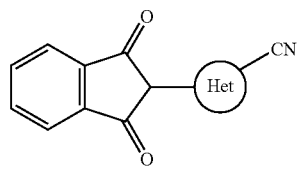

in which $R^1$ is as previously defined, with a reagent capable of hydrolysing a nitrile moiety, for example sodium hydroxide, in the presence of a solvent, for example water, at a temperature in the range of 0° C. to the boiling point of the solvent used.

Compounds of Formula 5 may be synthesised by reaction of a compound of Formula 6:

Formula 6

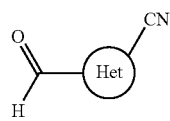

in which $R^1$ is as previously defined, with a compound of Formula 7:

Formula 7

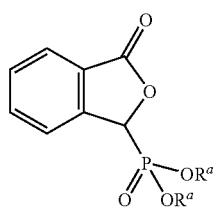

in which $R_a$ is a $C_{1-4}$ alkyl group, in the presence of a base, for example triethylamine or lithium hexamethyldisilazide, in a solvent, for example tetrahydrofuran, at a temperature in the range of −80° C. to the boiling point of the solvent used.

Compounds of Formula 7 may be synthesised by methods analogous to those described in WO 02/26576.

Compounds of Formula 4 may also be directly synthesised from compounds of Formula 7, by reacting them with a compound of Formula 8:

Formula 8

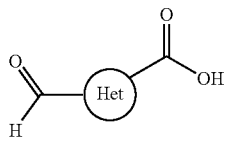

in the presence of a base, for example triethylamine or lithium hexamethyldisilazide, in a solvent, for example tetrahydrofuran, at a temperature in the range of −80° C. to the boiling point of the solvent used.

Compounds of Formula 6, where Het is:

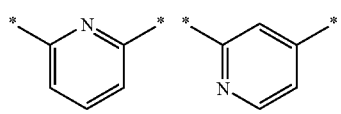

can be synthesised from compounds of Formula 9:

Formula 9

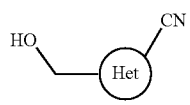

by oxidation of the hydroxy group with, for example, DMSO, dicyclohexylcarbodiimide (DCC) and anhydrous phosphoric acid.

Compounds of Formula 9 can be synthesised from compounds of Formula 10:

Formula 10

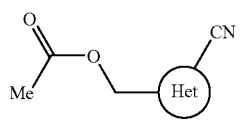

by removal of the acetyl group using an acid, such as dilute sulphuric acid, in an organic solvent, for example, THF.

The compounds of Formula 10 can be synthesised from the respective compounds of Formulae 11a and 11b:

Formula 11a

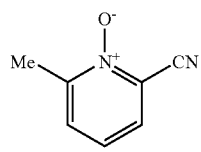

Formula 11b

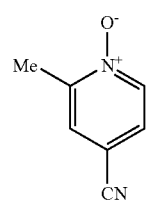

by addition to a pre-heated solution of acetic anhydride.

The compounds of Formulae 11a and 11b can be synthesised from compounds of Formulae 12a and 12b respectively:

Formula 12a

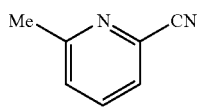

Formula 12b

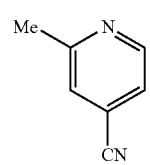

by oxidation, for example by m-chloroperoxybenzoic acid (m-CPBA) in an organic solvent, such as DCM.

The compound of Formula 12a can be synthesised from a compound of Formula 13:

Formula 13

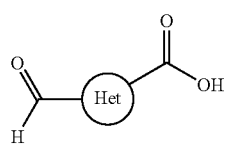

by first reaction with iodomethane, followed by dropwise addition of aqueous potassium cyanide to an ethanol-water solution of the product of the first step.

The compound of Formula 12b can be synthesised from a compound of Formula 13 by first reaction with iodoethane, followed by dropwise addition of aqueous potassium cyanide to an ethanol-water solution of the product of the first step.

Compounds of Formula 8:

Formula 8

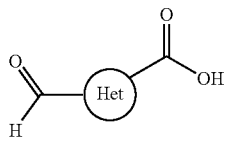

where Het is selected from:

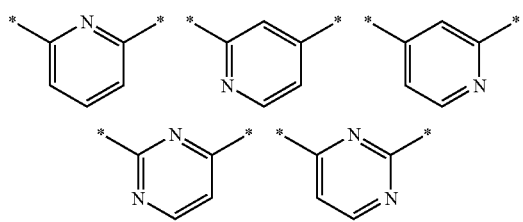

can be synthesised from compounds of Formula 14:

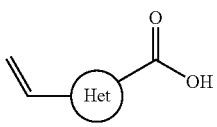

Formula 14 by oxidation of the alkene, for example, using ozone in a solution of the compound of Formula 14 in methanol and DCM (1:1) at −78° C.

Compounds of Formula 14 where Het is:

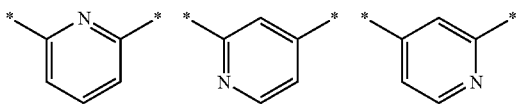

can be synthesised from compounds of Formula 15:

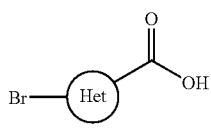

Formula 15 by Suzuki coupling with a compound of, for example, Formula 16:

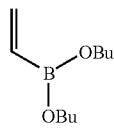

Formula 16 under the usual conditions.

The compounds of Formula 15 can be synthesised from compounds of Formula 17:

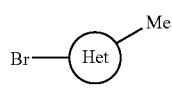

Formula 17 by oxidation, for example, using potassium permanganate in aqueous solution.

Compounds of Formula 14:

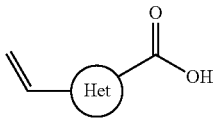

Formula 14 where Het is:

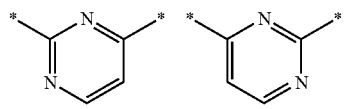

can be synthesised from compounds of Formula 18:

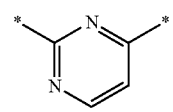

Formula 18 by hydrolysis of the cyano group, by, for example, sodium hydroxide in methanol.

The compound of Formula 18 where Het is:

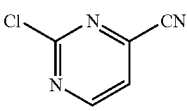

can be synthesised from a compound of Formula 19:

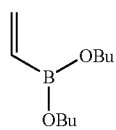

Formula 19 by Suzuki coupling with a compound of, for example, Formula 16:

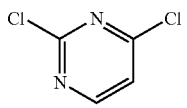

Formula 16 under the usual conditions.

The compound of Formula 19 can be synthesised from a compound of Formula 20:

Formula 20 by reaction with sodium cyanide in an organic solvent, for example, DMF.

The compound of Formula 18 where Het is:

[structure: pyrimidine with * at 2 and 4 positions]

can be synthesised from a compound of Formula 21:

[structure: 2-vinyl-4-chloropyrimidine] Formula 21 by reaction with sodium cyanide in an organic solvent, for example, DMF.

The compound of Formula 21 can be synthesised from a compound of Formula 20:

[structure: 2,4-dichloropyrimidine] Formula 20 by Suzuki coupling with a compound of, for example, Formula 16:

[structure: vinyl boronic acid dibutyl ester] Formula 16 under the usual conditions.

Compounds of Formula 8:

[structure: Het with CHO and COOH substituents] Formula 8 where Het is:

[structure: 5-fluoropyridine with * at 2 and 4 positions]

can be synthesised from a compound of Formula 22:

[structure: pyridine with dioxolane, F, and COOH] Formula 22 by deprotection of the aldehyde group using, for example, a mixture of acetone and water with a catalytic amount of pyridinium paratoluenesulfonate.

The compound of Formula 22 can be synthesised from a compound of Formula 23:

[structure: pyridine with dioxolane and F] Formula 23 by reaction with a strong base, e.g. lithium diisopropyl amide (LDA), followed by addition of $CO_2$. This reaction may, for example, be carried out at −78° C. in THF, where the $CO_2$ is added as dry ice.

The compound of Formula 23 can be synthesised from the compound of Formula 24:

[structure: 5-fluoro-2-formylpyridine] Formula 24 by protection of the aldehyde group, for example, by reaction with ethylene glycol (e.g. 1.5 equivalents) in the presence of a catalytic amount of paratoluenesulfonic acid in toluene, under relfux in a Dean-stark apparatus.

The compound of Formula 24 can be synthesised from a compound of Formula 25:

[structure: 2-bromo-5-fluoropyridine] Formula 25 by reaction with a strong base, e.g. butyl lithium, followed by addition of DMF. This reaction may, for example, be carried out at −78° C.

Compounds of Formula 8:

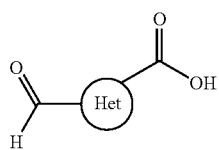

Formula 8 where Het is selected from:

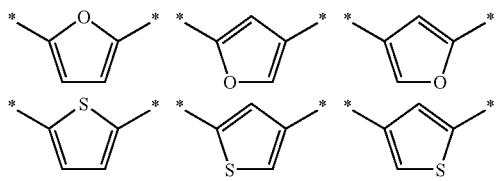

are commercially available or readily synthesisable.

Compounds of Formula 1 may also be synthesised by methods analogous to those described above in which the nitrile moiety in all Formulae is replaced by other moieties capable of generating a carboxylic acid, for example ester or carboxamide moieties.

Compounds of the present invention in which X is NH can be represented by Formula 26:

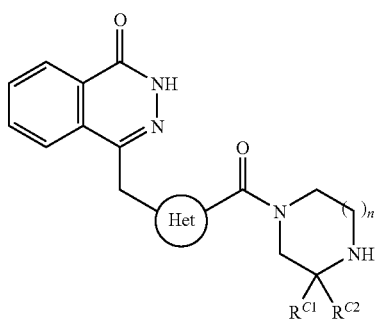

Formula 26 in which n, $R^{C1}$, $R^{C2}$ and $R^1$ are as previously defined. These compounds may be used to generate libraries of compounds of the invention as described below.

Compounds of the present invention in which X is $NR^X$, in which $R^X$ is an acyl moiety, and which may therefore be represented by Formula 27:

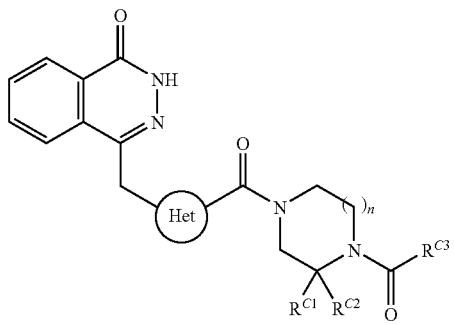

Formula 27 in which n, $R^{C1}$, $R^{C2}$ and $R^1$ are as previously defined and $R^{C3}$ is selected from the group consisting of optionally substituted $C_{1-20}$ alkyl, $C_{5-20}$ aryl and $C_{3-20}$ heterocyclyl, may be synthesised by reaction of a compound of Formula 26 with a compound of Formula $R^{C3}COX$, in which $R^{C3}$ is as previously defined and X is a suitable leaving group, for example a halogen such as chloro, optionally in the presence of a base, for example pyridine, triethylamine or diisopropylethylamine, optionally in the presence of a solvent, for example dichloromethane, at a temperature in the range of 0° C. to the boiling point of the solvent used.

Compounds of Formula $R^{C3}COX$ are commercially available or may be synthesised by methods reported in the chemical literature.

Compounds of Formula 27 may also be synthesised by reaction of a compound of Formula 26 with a compound of Formula $R^{C3}CO_2H$, in which $R^{C3}$ is as previously defined, in the presence of a coupling reagent system, for example 2-(1H-benzotriazol-1-yl)-1,1,3,3-tetramethyluronium tetrafluoroborate, 2-(1H-benzotriazol-1-yl)-1,1,3,3-tetramethyluronium hexafluorophosphate or (dimethylaminopropyl)ethylcarbodiimide hydrochloride/hydroxybenzotriazole, in the presence of a base, for example diisopropylethylamine, in a solvent, for example dimethylacetamide or dichloromethane, at a temperature in the range of 0° C. to the boiling point of the solvent used.

Compounds of Formula $R^{C3}CO_2H$ are commercially available or may be synthesised by methods reported in the chemical literature.

Compounds of the present invention in which X is $NR^X$, in which $R^X$ is an amido or thioamido moiety, and which may therefore be represented by Formula 28:

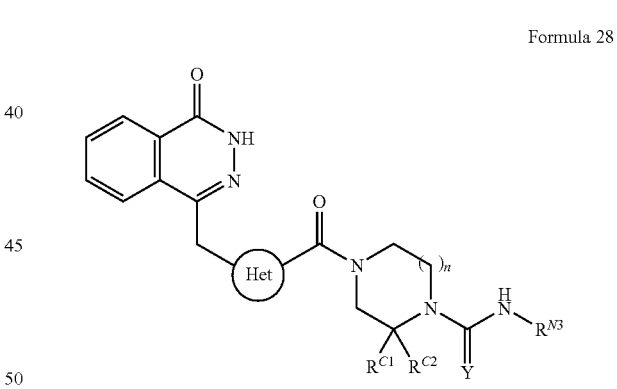

Formula 28 in which n, $R^{C1}$, $R^{C2}$ and $R^1$ are as previously defined, Y is O or S and $R^{N3}$ is selected from the group consisting of optionally substituted $C_{1-20}$ alkyl, $C_{5-20}$ aryl and $C_{3-20}$ heterocyclyl, may be synthesised by reaction of a compound of Formula 26 with a compound of Formula $R^{N3}NCY$, in which Y and $R^{N3}$ are as previously defined, in the presence of a solvent, for example dichloromethane, at a temperature in the range of 0° C. to the boiling point of the solvent used.

Compounds of Formula $R^{N3}NCY$ are commercially available or may be synthesised by methods reported in the chemical literature.

Compounds of the present invention in which X is $NR^X$, in which $R^X$ is a sulfonyl moiety, and which may therefore be represented by Formula 29:

Formula 29

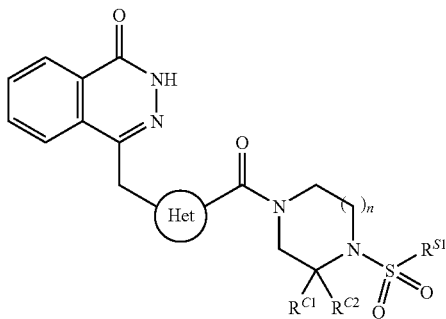

in which n, $R^{C1}$, $R^{C2}$ and $R^1$ are as previously defined and $R^{S1}$ is selected from the group consisting of optionally substituted $C_{1-20}$ alkyl, $C_{5-20}$ aryl and $C_{3-20}$ heterocyclyl, may be synthesised by reaction of a compound of Formula 26 with a compound of Formula $R^{S1}SO_2Cl$, in which $R^{S1}$ is as previously defined, optionally in the presence of a base, for example pyridine, triethylamine or diisopropylethylamine, in the presence of a solvent, for example dichloromethane, at a temperature in the range of 0° C. to the boiling point of the solvent used.

Compounds of Formula $R^{S1}SO_2Cl$ are commercially available or may be synthesised by methods reported in the chemical literature.

Compounds of the present invention in which X is $NR^X$, in which $R^X$ is selected from the group consisting of optionally substituted $C_{1-20}$ alkyl or $C_{3-20}$ heterocyclyl, and which may therefore be represented by Formula 30:

Formula 30

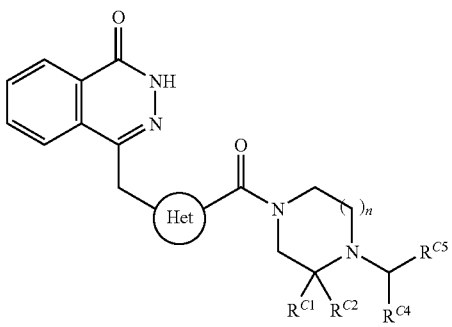

in which n, $R^{C1}$, $R^{C2}$ and $R^1$ are as previously defined and $R^{C4}$ and $R^{C5}$ are each individually selected from the group consisting of H, optionally substituted $C_{1-20}$ alkyl, $C_{5-20}$ aryl, $C_{3-20}$ heterocyclyl, or may together form an optionally substituted $C_{3-7}$ cycloalkyl or heterocyclyl group, may be synthesised by reaction of a compound of Formula 26 with a compound of Formula $R^{C4}COR^{C5}$, in which $R^{C4}$ and $R^{C5}$ are as previously defined, in the presence of a reducing agent, for example sodium cyanoborohydride or sodium triacetoxyborohydride, in the presence of a solvent, for example methanol, optionally in the presence of an acid catalyst, for example acetic acid, at a temperature in the range of 0° C. to the boiling point of the solvent used.

Compounds of Formula $R^{C4}COR^{C5}$ are commercially available or may be synthesised by methods reported in the chemical literature.

Use

The present invention provides active compounds, specifically, active in inhibiting the activity of PARP.

The term "active" as used herein, pertains to compounds which are capable of inhibiting PARP activity, and specifically includes both compounds with intrinsic activity (drugs) as well as prodrugs of such compounds, which prodrugs may themselves exhibit little or no intrinsic activity.

One assay which may conveniently be used in order to assess the PARP inhibition offered by a particular compound is described in the examples below.

The present invention further provides a method of inhibiting the activity of PARP in a cell, comprising contacting said cell with an effective amount of an active compound, preferably in the form of a pharmaceutically acceptable composition. Such a method may be practised in vitro or in vivo.

For example, a sample of cells may be grown in vitro and an active compound brought into contact with said cells, and the effect of the compound on those cells observed. As examples of "effect", the amount of DNA repair effected in a certain time may be determined. Where the active compound is found to exert an influence on the cells, this may be used as a prognostic or diagnostic marker of the efficacy of the compound in methods of treating a patient carrying cells of the same cellular type.

The term "treatment", as used herein in the context of treating a condition, pertains generally to treatment and therapy, whether of a human or an animal (e.g. in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e. prophylaxis) is also included.

The term "adjunct" as used herein relates to the use of active compounds in conjunction with known therapeutic means. Such means include cytotoxic regimens of drugs and/or ionising radiation as used in the treatment of different cancer types. In particular, the active compounds are known to potentiate the actions of a number of cancer chemotherapy treatments, which include the topoisomerase class of poisons and most of the known alkylating agents used in treating cancer.

Active compounds may also be used as cell culture additives to inhibit PARP, for example, in order to sensitize cells to known chemotherapeutic agents or ionising radiation treatments in vitro.

Active compounds may also be used as part of an in vitro assay, for example, in order to determine whether a candidate host is likely to benefit from treatment with the compound in question.

Administration

The active compound or pharmaceutical composition comprising the active compound may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly.

The subject may be a eukaryote, an animal, a vertebrate animal, a mammal, a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutang, gibbon), or a human.

Formulations

While it is possible for the active compound to be administered alone, it is preferable to present it as a pharmaceutical composition (e.g., formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing at least one active compound, as defined above, together with one or more pharmaceutically acceptable carriers, excipients, buffers, adjuvants, stabilisers, or other materials, as described herein.

The term "pharmaceutically acceptable" as used herein pertains to compounds, materials, compositions, and/or dosage forms which are, within the scope of sound medical judgement, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, diluents, excipients, etc. can be found in standard pharmaceutical texts. See, for example, "Handbook of Pharmaceutical Additives", 2nd Edition (eds. M. Ash and I. Ash), 2001 (Synapse Information Resources, Inc., Endicott, New York, USA), "Remington's Pharmaceutical Sciences", 20th edition, pub. Lippincott, Williams & Wilkins, 2000; and "Handbook of Pharmaceutical Excipients", 2nd edition, 1994.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Formulations may be in the form of liquids, solutions, suspensions, emulsions, elixirs, syrups, tablets, losenges, granules, powders, capsules, cachets, pills, ampoules, suppositories, pessaries, ointments, gels, pastes, creams, sprays, mists, foams, lotions, oils, boluses, electuaries, or aerosols.

Formulations suitable for oral administration (e.g., by ingestion) may be presented as discrete units such as capsules, cachets or tablets, each containing a predetermined amount of the active compound; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means, e.g. compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate); lubricants (e.g. magnesium stearate, talc, silica); disintegrants (e.g. sodium starch glycolate, cross-linked povidone, cross-linked sodium carboxymethyl cellulose); surface-active or dispersing or wetting agents (e.g., sodium lauryl sulfate); and preservatives (e.g., methyl p-hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with an enteric coating, to provide release in parts of the gut other than the stomach.

Formulations suitable for topical administration (e.g. transdermal, intranasal, ocular, buccal, and sublingual) may be formulated as an ointment, cream, suspension, lotion, powder, solution, past, gel, spray, aerosol, or oil. Alternatively, a formulation may comprise a patch or a dressing such as a bandage or adhesive plaster impregnated with active compounds and optionally one or more excipients or diluents.

Formulations suitable for topical administration in the mouth include losenges comprising the active compound in a flavored basis, usually sucrose and acacia or tragacanth; pastilles comprising the active compound in an inert basis such as gelatin and glycerin, or sucrose and acacia; and mouthwashes comprising the active compound in a suitable liquid carrier.

Formulations suitable for topical administration to the eye also include eye drops wherein the active compound is dissolved or suspended in a suitable carrier, especially an aqueous solvent for the active compound.

Formulations suitable for nasal administration, wherein the carrier is a solid, include a coarse powder having a particle size, for example, in the range of about 20 to about 500 microns which is administered in the manner in which snuff is taken, i.e. by rapid inhalation through the nasal passage from a container of the powder held close up to the nose. Suitable formulations wherein the carrier is a liquid for administration as, for example, nasal spray, nasal drops, or by aerosol administration by nebuliser, include aqueous or oily solutions of the active compound.

Formulations suitable for administration by inhalation include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for topical administration via the skin include ointments, creams, and emulsions. When formulated in an ointment, the active compound may optionally be employed with either a paraffinic or a water-miscible ointment base. Alternatively, the active compounds may be formulated in a cream with an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

When formulated as a topical emulsion, the oily phase may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Dosage

It will be appreciated that appropriate dosages of the active compounds, and compositions comprising the active compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician.

In general, a suitable dose of the active compound is in the range of about 100 µg to about 250 mg per kilogram body weight of the subject per day. Where the active compound is a salt, an ester, prodrug, or the like, the amount administered is calculated on the basis of the parent compound and so the actual weight to be used is increased proportionately.

EXAMPLES

General Experimental Methods

Preparative HPLC

Samples were purified with a Waters mass-directed purification system utilising a Waters 600 LC pump, Waters Xterra C18 column (5 µm 19 mm×50 mm) and Micromass ZQ mass spectrometer, operating in positive ion electrospray ionisation mode. Mobile phases A (0.1% formic acid in water) and B (0.1% formic acid in acetonitrile) were used in a gradient; 5% B to 100% over 7 min, held for 3 min, at a flow rate of 20 ml/min.

Analytical HPLC-MS

Analytical HPLC was typically carried out with a Spectra System P4000 pump and Jones Genesis C18 column (4 µm, 50 mm×4.6 mm). Mobile phases A (0.1% formic acid in water) and B (acetonitrile) were used in a gradient of 5% B for 1 min rising to 98% B after 5 min, held for 3 min at a flow rate of 2 ml/min. Detection was by a TSP UV 6000LP detector at 254 nm UV and range 210-600 nm PDA. The Mass spectrometer was a Finnigan LCQ operating in positive ion electrospray mode.

NMR $^1$H NMR and $^{13}$C NMR were typically recorded using Bruker DPX 300 spectrometer at 300 MHz and 75 MHz respectively. Chemical shifts were reported in parts per million (ppm) on the δ scale relative to tetramethylsilane internal standard. Unless stated otherwise all samples were dissolved in DMSO-$d_6$.

Synthesis of Key Intermediates (i) Synthesis of (3-oxo-1,3-dihydro-isobenzofuran-1-yl)-phosphonic acid dimethyl ester

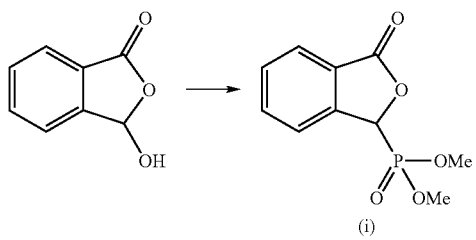

Dimethyl phosphite (22.0 g, 0.2 mol) was added drop-wise to a solution of sodium methoxide (43.0 g) in methanol (100 ml) at 0° C. 2-Carboxybenzaldehyde (21.0 g, 0.1 mol) was then added portion-wise to the reaction mixture as a slurry in methanol (40 ml), with the temperature kept below 5° C. The resulting pale yellow solution was warmed to 20° C. over 1 hour. Methanesulphonic acid (21.2 g, 0.22 mol) was added to the reaction drop-wise and the resulting white suspension was evaporated in vacuo. The white residue was quenched with water, extracted with chloroform (3×100 ml). The combined organic extracts was washed with water (2×100 ml), dried over MgSO$_4$, and evaporated in vacuo to yield (i) as a white solid (32.0 g, 95%, 95% purity). This was then used without further purification in the next stage.

(ii) Synthesis of Aldehyde Intermediates

6-Formyl-pyridine-2-carboxylic acid (iia)

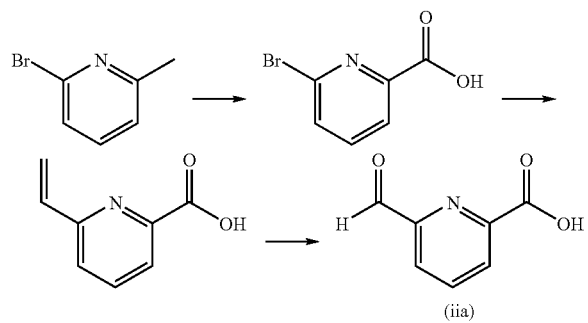

(a) To 6-bromo-2-methyl-pyridine in water was added 1 equivalent of potassium permanganate. The solution was heated up at reflux for 2 hours. The reaction was followed and potassium permanganate was added until no starting material remained. After cooling down, the solution was filtered and the solution was acidified until pH=3. The precipitate was filtered and dried.

(b) A solution of 6-bromo-2-pyridine-carboxylic acid, 1.5 equivalents of vinylboronic acid dibutyl ester, 1.2 equivalents of potassium carbonate in DMA/water 9/1 was degassed for twenty minutes, then 0.06 equivalent of palladium tetrakis were added, the suspension degassed for a further thirty seconds and the suspension heated up in the microwave at 170° C. for twenty five minutes. The resulting suspension was filtered through a pad of silica gel and the filtrate concentrated.

(c) A solution of 6-vinyl-pyridine-2-carboxylic acid in methanol/DCM 1/1 was cooled to −78° C. and ozone bubbled through it until the solution becomes blue. A stream of nitrogen is then passed through to remove the ozone excess and 1.5 equivalent of methyl sulfide added. The solution was allowed to warm up to room temperature and was concentrated. The product (iia) was then purified by silica flash chromatography.

6-Formyl-pyridine-2-carbonitrile (iib)

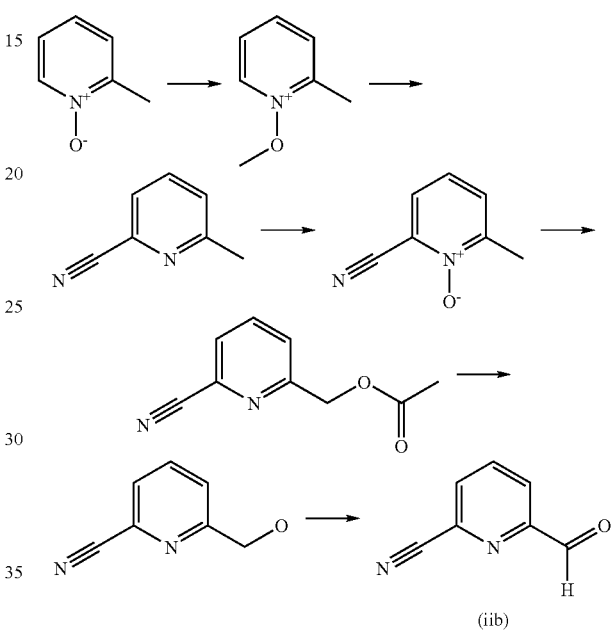

(a) Iodomethane (204 ml, 3.1 mol) was added drop-wise to 2-picoline-N-oxide (100 g, 0.9 mol) over 1 hour at 25° C. The reaction was left standing for 12 hours. The reaction mixture was filtered, washed with Et$_2$O, and dried in a vacuum oven for 3 hours to yield the product which was taken towards the next step without purification.

(b) A solution of aqueous KCN (112.0 g, 1.7 mol in 250 ml of H$_2$O) was added dropwise to an ethanol-H$_2$O solution of the product of the previous step (7:3) at 0° C. over 180 minutes. The reaction was left to stir for a further 30 minutes. The reaction was then warmed to 25° C., extracted into 200 ml and a further 4×100 ml of dichloromethane. The combined organic layers was washed with 200 ml saturated brine, dried with MgSO$_4$, filtered and evaporated to yield a dark red liquid (51.0 g) which was left to crystallize on standing for 12 hours. The solid was filtered, washed with cold hexane (2×50 ml) and air-dried. The solid was then purified by column chromatography (70 g silica, hexane:ethyl acetate) to yield the product as white solid (7.0 g, 7%). m/z [M+1]$^+$ 119 (98% purity)

(c) m-CPBA (16.2 g, 0.14 mol) was added to a solution of the product of the previous step (52.0 g, 0.15 mmol) in DCM (50 ml) and the reaction was left to stir for 12 hours. Na$_2$S$_2$O$_3$ (21.5 g) was added and the reaction mixture was left to stir for a further 30 minutes. The reaction was then filtered, washed with saturated NaHCO$_3$ (2×30 ml), brine (2×30 ml), dried with MgSO$_4$, filtered and evaporated to yield the product as a white solid (13.6 g, 73.8%) which was taken towards the next step without purification.

(d) The product of the previous step was added (13.5 g, 101.3 mmol) to a pre-heated solution of acetic anhydride (60 ml) at 120° C. and the reaction was refluxed for 90 minutes. 60 ml of ethanol was then added cautiously to the reaction mixture, refluxed for a further 10 minutes and cooled to 25° C. The reaction was added to water (100 ml) and neutralised with NaHCO$_3$ (50 g). The reaction was extracted into diethyl ether (2×30 ml). The combined organic layers was washed with water (2×20 ml) and dried with MgSO$_4$, filtered and evaporated to yield a brown oil which was purified by column chromatography (hexane:ethyl acetate) to yield the product as a yellow oil (5.4 g, 30%). m/z [M+1]$^+$ 177 (30% purity)

(e) 1N H$_2$SO$_4$ (6 ml) was added to a solution of the product of the previous step (5.4 g, 30.6 mmol) in tetrahydrofuran (15 ml) and reaction was refluxed for 18 hours. The reaction was cooled, poured into water (150 ml), neutralised with NaHCO$_3$ and extracted into DCM (3×50 ml). The combined organic layers was washed with 100 ml saturated brine, dried with MgSO$_4$, filtered and evaporated to yield the product as a brown solid which was taken towards the next step without purification. m/z [M+1]$^+$ 134 (71% purity)

(f) The product of the previous step and N,N'-dicyclohexylcarbodiimide (19.3 g, 93.0 mmol) were added to a mixture of DMSO (22 ml) & anhydrous H$_3$PO$_4$ (1.4 g) and the reaction was left to stir 1.5 hours. The reaction was filtered and washed with diethyl ether (2×30 ml) and water (2×30 ml). The reaction layers was separated and the organic layer was washed with saturated brine (2×30 ml), dried with MgSO$_4$, filtered and evaporated to yield (iib) as a yellow solid which was taken towards the next step without purification.

2-Formyl-isonicotinic acid (iic)

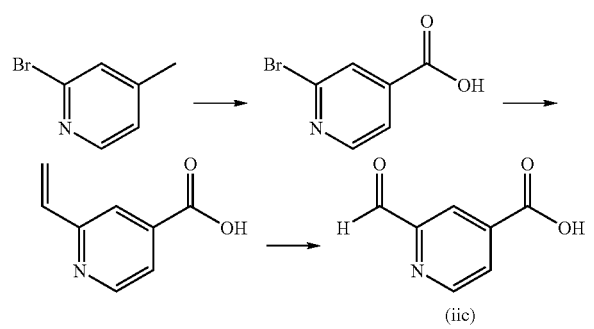

(iic)

(a) To 2-bromo-4-methyl-pyridine in water was added 1 equivalent of potassium permanganate. The solution was heated up at reflux for 2 hours. The reaction was followed and potassium permanganate was added until no starting material remained. After cooling down, the solution was filtered and the solution was acidified until pH=3. The precipitate was filtered and dried.

(b) A solution of 2-bromo-isonicotinic acid, 1.5 equivalents of vinylboronic acid dibutyl ester, 1.2 equivalents of potassium carbonate in DMA/water 9/1 was degassed for twenty minutes, then 0.06 equivalent of palladium tetrakis were added, the suspension degassed for a further thirty seconds and the suspension heated up in the microwave at 170° C. for twenty five minutes. The resulting suspension was filtered through a pad of silica gel and the filtrate concentrated.

(c) A solution of 2-vinyl-isonicotinic acid in methanol/DCM 1/1 was cooled to −78° C. and ozone bubbled through it until the solution becomes blue. A stream of nitrogen is then passed through to remove the ozone excess and 1.5 equivalent of methyl sulfide added. The solution was allowed to warm up to room temperature and was concentrated. The product (iic) was then purified by silica flash chromatography.

2-Formyl-isonicotinonitrile (iid)

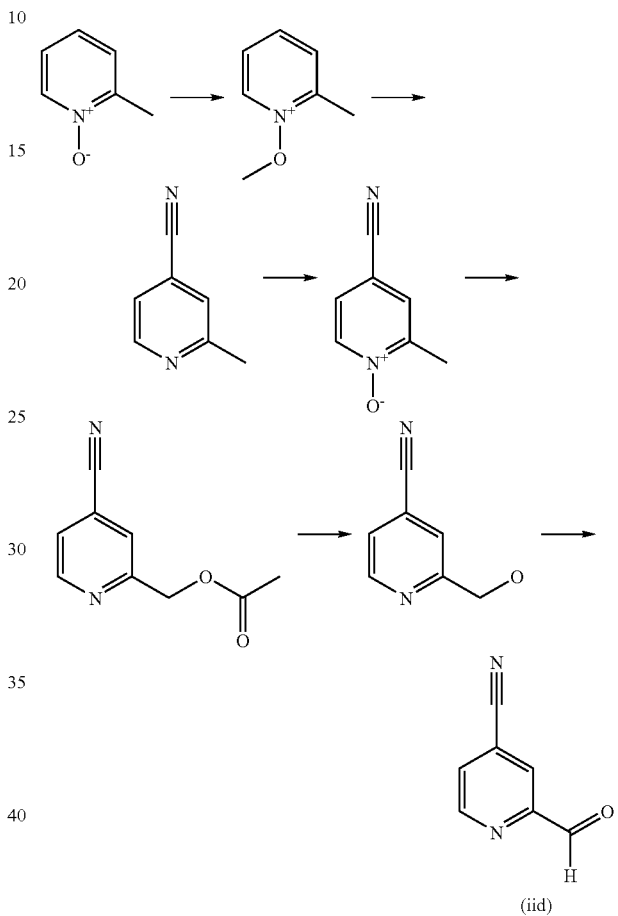

(iid)

(a) Iodoethane (265 ml, 3.3 mol) was added drop-wise to 2-picoline-N-oxide (100 g, 0.9 mol) over 1 hour at 25° C. The reaction was left standing for 12 hours. The reaction mixture was filtered, washed with Et$_2$O, and dried in a vacuum oven for 3 hours to yield the product which was taken towards the next step without purification.

(b) A solution of aqueous KCN (52.0 g, 0.8 mol in 100 ml of H$_2$O) was added dropwise to a ethanol-H$_2$O solution of the product of the previous step (7:3) at 50° C. over 110 minutes. The reaction was left to stir for a further 30 minutes. The reaction was then warmed to 25° C., extracted into 200 ml and a further 4×100 ml of dichloromethane. The combined organic layers was washed with 200 ml saturated brine, dried with MgSO$_4$, filtered and evaporated to yield a dark red liquid (51.0 g). This procedure was repeated and combined to yield a total of 102.0 g of the reaction mixture which was purified by column chromatography (360 g silica, hexane:ethyl acetate) to yield the product as a white solid (10.6 g, 10%). m/z [M+1]$^+$ 119 (98% purity)

(c) m-CPBA (27.7 g, 80.2 mmol) was added to a solution of the product of the previous step (8.6 g, 72.8 mmol) in DCM (30 ml) and the reaction was left to stir for 12 hours. Na$_2$S$_2$O$_3$ (10.0 g, 16.0 mmol) was added and the reaction mixture was left to stir for a further 30 min. The reaction was then filtered, washed with saturated NaHCO₃ (2×30 ml), brine (2×30 ml), dried with MgSO₄, filtered and evaporated in vacuo to yield the product as a white solid (6.5 g, 67%) which was taken towards the next step without purification.

(d) The product of the previous step was added (8.0 g, 60.0 mmol) to a pre-heated solution of acetic anhydride (30 ml) at 120° C. and the reaction was refluxed for 90 minutes. 30 ml of ethanol was then added cautiously to the reaction mixture, refluxed for a further 10 minutes and cooled to 25° C. The reaction was added to water (100 ml) and neutralised with NaHCO₃ (50 g). The reaction was extracted into diethyl ether (2×30 ml). The combined organic layers was washed with water (2×20 ml) and dried with MgSO₄, filtered and evaporated in vacuo to yield a brown oil which was purified by column chromatography (hexane:ethyl acetate) to yield the product as a yellow solid (4.0 g, 38%). m/z [M+1]⁺ 177 (96% purity)

(e) 1N H₂SO₄ (16 ml) was added to a solution of the product of the previous step (2.7 g, 15.6 mmol) in tetrahydrofuran (25 ml) and reaction was refluxed for 18 hours. The reaction was cooled, poured into water (150 ml), neutralised with NaHCO₃ and extracted into DCM (3×50 ml). The combined organic layers was washed with 100 ml saturated brine, dried with MgSO₄, filtered and evaporated in vacuo to yield the product as a yellow solid (1.4 g, 67%) which was taken towards the next step without purification.

(f) The product of the previous step (1.4 g, 10.2 mmol) and N,N'-dicyclohexylcarbodiimide (6.2 g, 30.0 mmol) were added to a mixture of DMSO (22 ml) & anhydrous H₃PO₄ (0.45 g) and the reaction was left to stir 1.5 hours. The reaction was filtered and washed with diethyl ether (2×30 ml) and water (2×30 ml). The reaction layers was separated and the organic layer was washed with saturated brine (2×30 ml), dried with MgSO₄, filtered and evaporated in vacuo to yield (iid) as a yellow solid which was taken towards the next step without purification.

(iii) Coupling of Aldehyde Intermediates (ii) to (3-oxo-1,3-dihydro-isobenzofuran-1-yl)-phosphonic acid dimethyl ester (i)

(a) Synthesis of 2-(3-oxo-3H-isobenzofuran-1-ylidenemethyl)-isonicotinic acid (iiia)

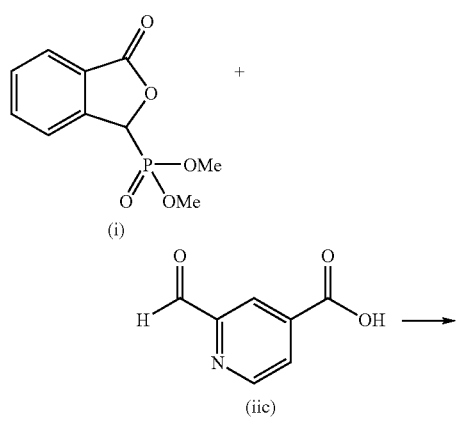

-continued

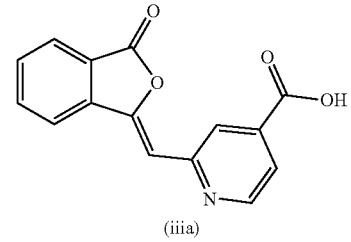

(iiia)

To a mixture of (3-oxo-1,3-dihydro-isobenzofuran-1-yl)-phosphonic acid dimethyl ester (i)(0.18 g, 0.77 mmol) and 2-formyl-isonicotinic acid (iic)(0.12 g, 0.77 mmol) in tetrahydrofuran (10 ml) was added triethylamine (0.32 ml, 2.8 mmol). The reaction mixture was stirred at 50° C. for 4 hours, then allowed to cool down to room temperature. The tetrahydrofuran was evaporated to half its volume, then a 1N HCl solution added until pH 3. Water was added until no more solid crashed out of solution. The white solid was filtered, washed with water, then hexane and recrystallised from acetonitrile. Amount: 0.9 g, m/z [M+1]⁺ 268 (90% purity)

All aldehydes containing a carboxylic acid function were coupled to (3-oxo-1,3-dihydro-isobenzofuran-1-yl)-phosphonic acid dimethyl ester using the conditions described above, except that the reaction was performed at room temperature for 16 hours instead of 50° C. for 4 hours.

Compounds synthesized following the above protocol are:
From 6-formyal-pyridine-2-carboxylic acid (iia), 6-[3-oxo-3H-isobenzofuran-1-ylidenemethyl]-pyridine-2-carboxylic acid (iiib)
From 5-formyl-furan-2-carboxylic acid, 5-(3-oxo-3H-isobenzofuran-1-ylidenemethyl)-thiophene-2-carboxylic acid (iiic): m/z [M+1]⁺ 287 (92% purity)
From 5-formyl-thiophen-2-carboxylic acid, 5-(3-oxo-3H-isobenzofuran-1-ylidenemethyl)-furan-2-carboxylic acid (iiid): m/z [M+1]⁺ 257 (90% purity)

(b) Alternative Synthesis of 2-(3-oxo-3H-isobenzofuran-1-ylidenemethyl)-isonicotinic acid (iiia)

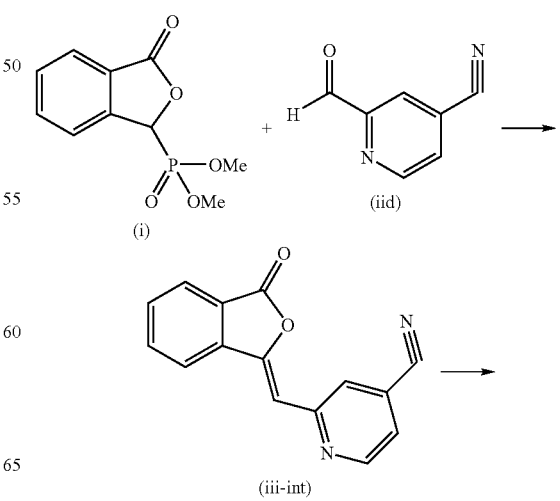

-continued

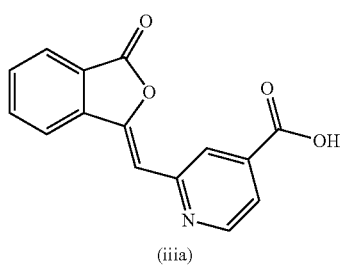
(iiia)

(i) Triethylamine (2.2 ml, 15 mmol) was added to a mixture of (3-oxo-1,3-dihydro-isobenzofuran-1-yl)-phosphonic acid dimethyl ester (i)(2.4 g, 10.2 mmol) and (iid) (10.2 mmol) in tetrahydrofuran (10 ml). The reaction mixture was stirred for over 12 hours at 25° C. and concentrated in vacuo to yield 2-[3-oxo-3H-isobenzofuran-(1E,Z)-ylidenemethyl]-isonicotinonitrile (iii-int) as a red solid which was taken towards the next step without purification.

(ii) A mixture of 2-[3-oxo-3H-isobenzofuran-(1E,Z)-ylidenemethyl]-isonicotinonitrile (iii-int)(10.2 mmol), water (50 ml) and potassium hydroxide pellets (1.7 g, 30.7 mmol) were refluxed for 16 hours. The reaction was cooled to 25° C. and washed with dichloromethane (2×30 ml). The aqueous layer was then concentrated in vacuo and the solid obtained (iiia) taken into the next step without further purification.

All aldehydes containing a nitrile group were coupled to (3-oxo-1,3-dihydro-isobenzofuran-1-yl)-phosphonic acid dimethyl ester, then hydrolysed to the carboxylic acid using the conditions described above.

Compounds synthesized following the above protocol are:
From 6-formyl-pyridine-2-carbonitrile (iib), 6-[3-oxo-3H-isobenzofuran-1-ylidenemethyl]-pyridine-2-carboxylic acid (iiib); step (a) gave a yellow solid: m/z [M+1]⁺ 249 (98% purity); step (b) gave a thick yellow oil: m/z [M+1]⁺ 286 (83% purity).

(c) 4-(3-Oxo-3H-isobenzofuran-1-ylidene methyl)-pyridine-2 carbonitrile (iii'e)

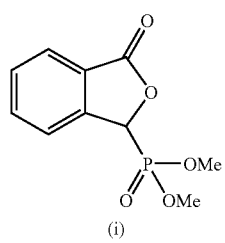
(i)

+

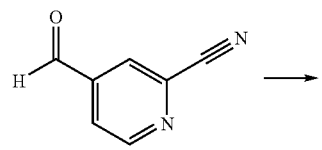

-continued

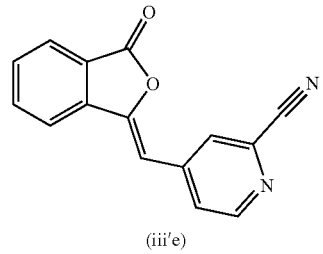
(iii'e)

To a solution of 4-formyl-pyridine-2-carbonitrile (4.89 g, 37.0 mmol) in anhydrous THF (200 mL) was added [(3-oxo-1,3-dihydro-isobenzofuran-1-yl)-phosphonic acid dimethyl ester]phosphonate (9.2 g, 37.0 mmol), triethylamine (5.1 mL, 37.0 mmol) was then added and the reaction stirred for 18 hrs at room temperature. The reaction mixture was then filtered and the solid isolated was washed with dry THF (2×25 mL) and dried in vacuo. Two peaks by LC-MS analysis (geometric isomers), (7.0 g, 76%); m/z (LC-MS, ESP), rt=4.19 mins, (M+H)=249 & rt=4.36 mins, (M+H)=249. This material was taken through without need for purification.

(iv) Conversion of Izobenzofuran Compounds to Phthalazinone Compounds

(a) Synthesis of 5-(4-oxo-3,4-dihydro-phthalazin-1-ylmethyl)-furan-2-carboxylic acid (iva)

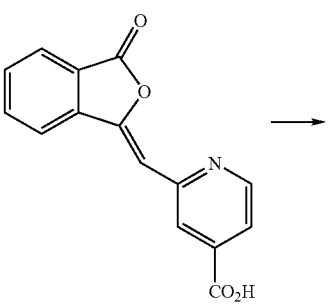
(iiia)

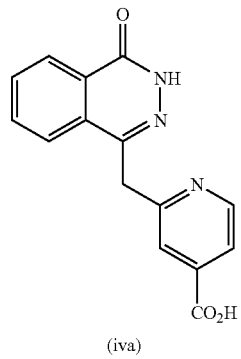
(iva)

To a suspension of 2-[3-oxo-3H-isobenzofuran-ylidenemethyl]isonicotinic acid (iiia)(87 mg, 0.32 mmol) in water (2 ml), was added hydrazine monohydrate (33 mg, 0.64 mmol) and the mixture heated up at reflux for 5 hours. The solution was concentrated to half its volume and acidified with a solution 1N HCl until pH 3. The white solid was filtered, washed with water and dried. Amount: 32 mg.

m/z [M+1]⁺ 282 (42% purity)

The phthalazinone core was formed on all compounds according to the protocol described above.

Compounds synthesized following the above protocol are:
From 6-[3-oxo-3H-isobenzofuran-1-ylidenemethyl]-pyridine-2-carboxylic acid (iiib), 6-(4-oxo-3,4-dihydro-phthalazin-1-ylmethyl)-pyridine-2-carboxylic acid (ivb): m/z [M+1]+ 282 (48% purity);
From 5-(3-oxo-3H-isobenzofuran-1-ylidenemethyl)-thiophene-2-carboxylic acid (iiic), 5-(4-oxo-3,4-dihydro-phthalazin-1-ylmethyl)-thiophene-2-carboxylic acid (ivc): m/z [M+1]+ 287 (60% purity);
From 5-(3-oxo-3H-isobenzofuran-1-ylidenemethyl)-furan-2-carboxylic acid (iiid), 5-(4-oxo-3,4-dihydro-phthalazin-1-ylmethyl)-furane-2-carboxylic acid (ivd): m/z [M+1]+ 271 (94% purity).

(b) Synthesis of 4-(4-Oxo-3,4-dihydro-phthalazin-1-ylmethyl)-pyridine-2-carboxylic acid (ive)

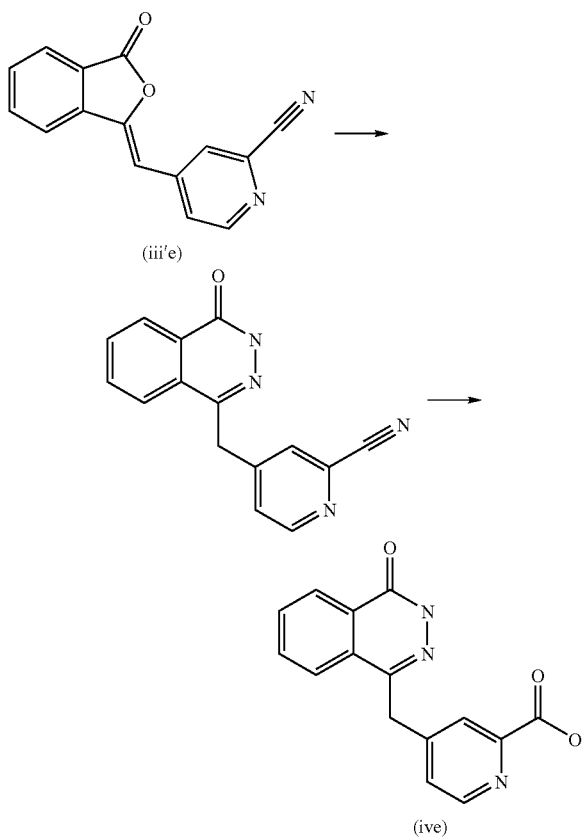

To 4-(3-oxo-3H-isobenzofuran-1-ylidene methyl)-pyridine-2 carbonitrile (iii'e)(3.72 g, 15.0 mmol) was added water (100 mL) and hydrazine monohydrate (1.5 g, 30.0 mmol). The reaction mixture was then heated to 100° C. for 6 hours and then cooled to room temperature. The white suspension was filtered and washed with diethyl ether (2×20 mL). The material was then dried in vacuo. Major peak by LC-MS analysis, (7.0 g, 76%); m/z (LC-MS, ESN), rt=3.54 mins (M+H)=261.

To a solution of the resulting material (2.36 g, 9.0 mmol) in ethanol (10 mL) was added conc hydrochloride acid (5 mL). The reaction mixture was then heated to 70° C. for 18 hours and then cooled to 5° C., the resultant white suspension was filtered and washed with water (2×5 mL) followed by diethyl ether (2×20 mL). A beige solid was isolated with major peak in LC-MS analysis, (2.40 g, 94%); m/z (LC-MS, ESP), RT=3.49 mins, (M+H)=282; & (2M+H)=563. The material was taken through without need for purification.

(v) Addition of Piperazine Group (a) Synthesis of 4-[6-(piperazine-1-carbonyl)-pyridin-2-ylmethyl]-2H-phthalazin-1-one (vb)

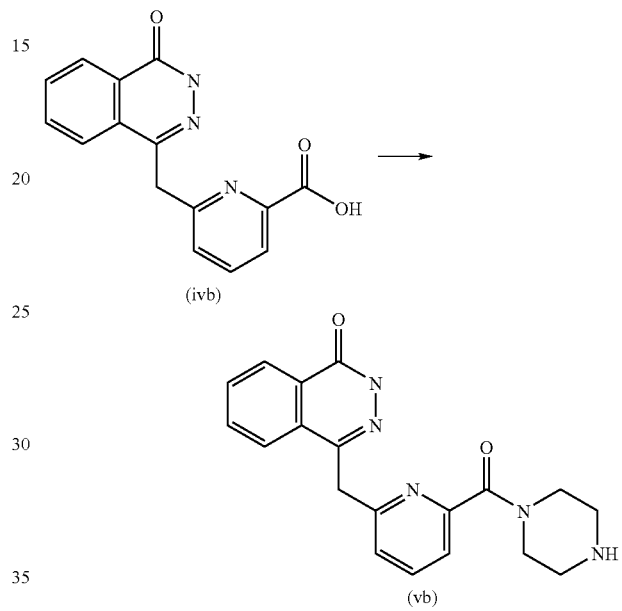

A mixture of 6-(4-oxo-3,4-dihydro-phthalazin-1-ylmethyl)-pyridine-2-carboxylic acid (ivb)(0.3 g, 1.1 mmol), triethylamine (0.3 ml, 2.1 mmol), tert-butyl-1-piperazine carboxylate (0.23 g, 1.3 mmol) and 2-(1H-benzotriazole-1-yl)-1,1,3,3-tetramethyluronium hexafluorophosphate (0.5 g, 1.3 mmol) in dimethylformamide (10 ml) was stirred for 18 hours. The reaction mixture was precipitated on the addition of water (50 ml) and air-dried. The white precipitate was dissolved in ethanol (3 ml) and 12 M hydrochloric acid (6 ml) was added to the solution and the reaction was stirred for 30 minutes. The reaction was then concentrated in vacuo, redissolved in water (10 ml) and washed with dichloromethane (2×10 ml). The aqueous layer was basified with ammonium hydroxide and extracted into dichloromethane (2×10 ml). The combined organic layers was dried with MgSO4, filtered and evaporated to yield the expected product (va) as a pink solid (0.23 g, 73%). m/z [M+1]+ 250 (96% purity)

All compounds were coupled to piperazine-1-carboxylic acid tert-butyl ester and had their protecting group removed according to the protocol described above.

Compounds synthesized following the above protocol are:
From 5-(4-oxo-3,4-dihydro-phthalazin-1-ylmethyl)-furan-2-carboxylic acid (iva), 4-[4-(piperazine-1-carbonyl)-pyridin-2-ylmethyl]-2H-phthalazin-1-one (va): m/z [M+1]+ 250 (96% purity);
From 5-(4-oxo-3,4-dihydro-phthalazin-1-ylmethyl)-thiophene-2-carboxylic acid (ivc), 4-[5-(piperazine-1-carbonyl)-thiophen-2-ylmethyl]-2H-phthalazin-1-one (vc): m/z [M+1]+ 339 (80% purity);

From 5-(4-oxo-3,4-dihydro-phthalazin-1-ylmethyl)-furane-2-carboxylic acid (ivd), 4-[5-(piperazine-1-carbonyl)-furan-2-ylmethyl]-2H-phthalazin-1-one (vd): m/z [M+1]+ 355 (84% purity).

(b) Synthesis of 4-[2-(piperazine-1-carbonyl)-pyridin-4-ylmethyl]-2H-phthalazin-1-one (ve)

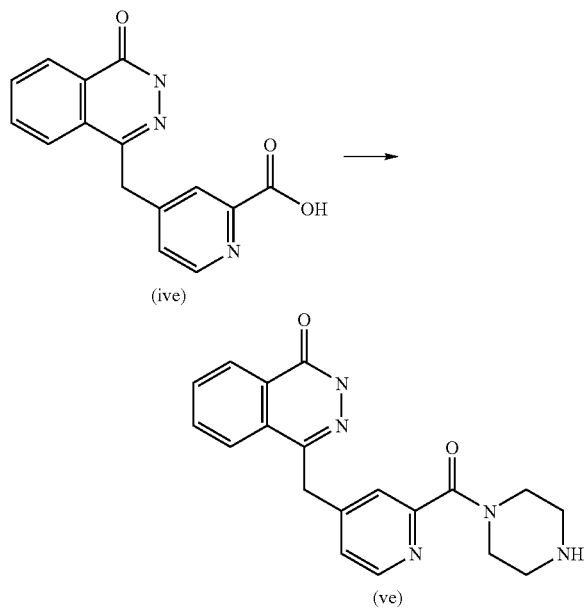

To a solution of 4-(4-oxo-3,4-dihydro-phthalazin-1-ylmethyl)-pyridine-2-carboxylic acid (ive)(0.563 g, 2/0 mmol) in anhydrous DCM (30 mL) was added tert-butyl 1-piperazinecarboxylate (0.45 g, 2.4 mmol) and O-benzotriazole-N,N,N',N'-tetramethyl-uronium-hexafluoro-phosphate (0.91 g, 2.4 mmol). The mixture was stirred for 5 minutes before N',N'-diisopropylethylamine (0.42 mL, 2.4 mmol) was added. After 30 minutes of stirring at room temperature the reaction mixture was filtered, and the concentrated in vacuo. The resultant oil was subjected to chromatography using EtOAc:MeOH 9:1 (rf of 0.23), a white solid was isolated. Single peak in LC-MS analysis, (0.71 g, 79%) and required no further purification. m/z (LC-MS, ESP), RT=3.75 min. (M+H)=450.

4M hydrogen chloride (3.25 mL, 13.0 mmol) was added to the resulting compound (0.60 g, 1.35 mmol) in dioxane. After 15 minutes the solvent was removed in vacuo and 7N ammonia in methanol (3 mL, 15.0 mmol) added. The resultant cream precipitate was filtered. The filtrate was concentrated in vacuo to afford a sticky gum (0.31 g 89% yield). LC-MS analysis 93% purity, no further purification attempted. m/z (LC-MS, ESP), RT=2.86 mins. (M+H)=350.

Example 1

The appropriate acid chloride or sulphonyl chloride (0.24 mmol) was added to a solution of 4-[4-(piperazine-1-carbonyl)-pyridin-2-ylmethyl]-2H-phthalazin-1-one (va) in dichloromethane (2 ml). Hunigs base (0.4 mmol) was then added and the reaction was stirred at room temperature for 16 hours. The reaction mixtures were then purified by preparative HPLC.

The compounds synthesised are set out below.

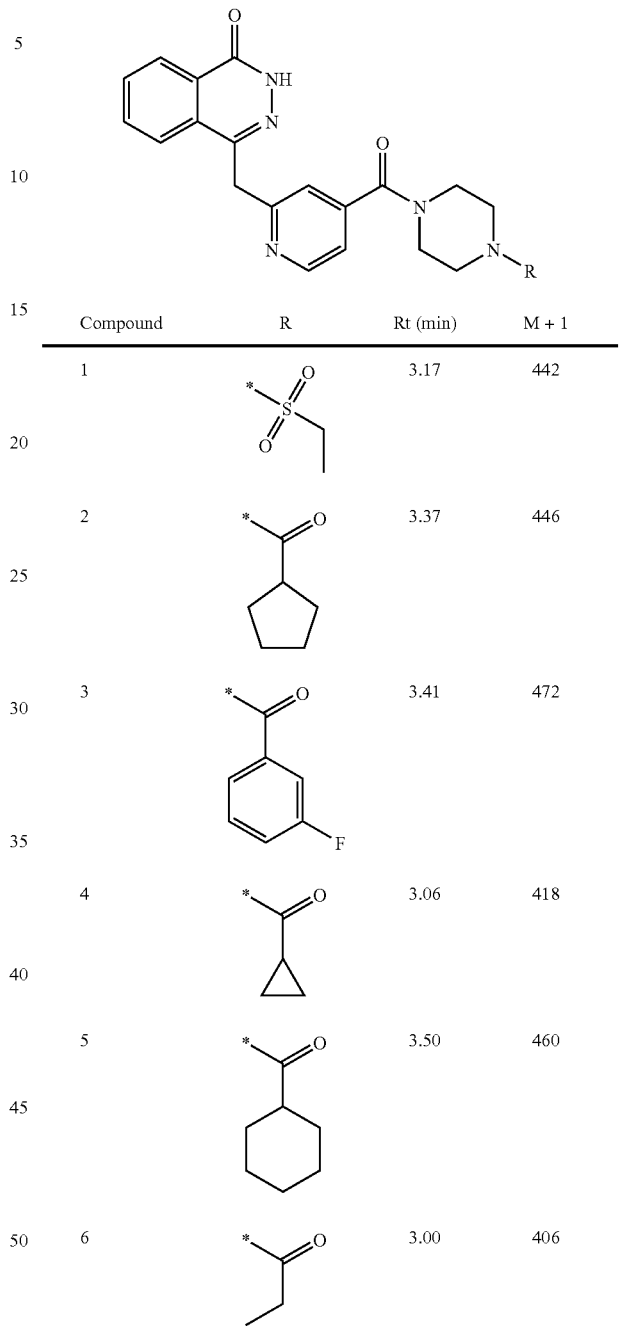

| Compound | R | Rt (min) | M + 1 |
|---|---|---|---|
| 1 | ethylsulfonyl | 3.17 | 442 |
| 2 | cyclopentylcarbonyl | 3.37 | 446 |
| 3 | 3-fluorobenzoyl | 3.41 | 472 |
| 4 | cyclopropylcarbonyl | 3.06 | 418 |
| 5 | cyclohexylcarbonyl | 3.50 | 460 |
| 6 | propanoyl | 3.00 | 406 |

Example 2

(a) The appropriate acid chloride or sulphonyl chloride (0.24 mmol) was added to a solution of 4-[4-(piperazine-1-carbonyl)-pyridin-2-yl methyl]-2H-phthalazin-1-one (vb) in dichloromethane (2 ml). Hunigs base (0.4 mmol) was then added and the reaction was stirred at room temperature for 16 hours. The reaction mixtures were then purified by preparative HPLC.

The compounds synthesised are set out below.

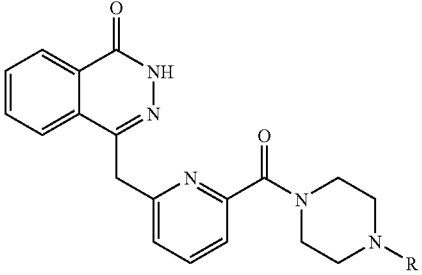

| Compound | R | Rt (min) | M + 1 |
|---|---|---|---|
| 7 | 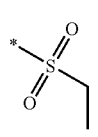 | 3.10 | 406 |
| 8 | 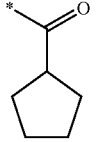 | 3.32 | 442 |
| 9 | 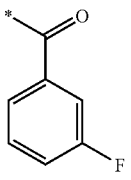 | 3.56 | 446 |
| 10 | 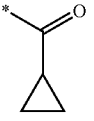 | 3.53 | 472 |
| 11 | 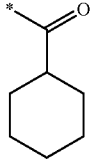 | 3.19 | 418 |
| 12 | 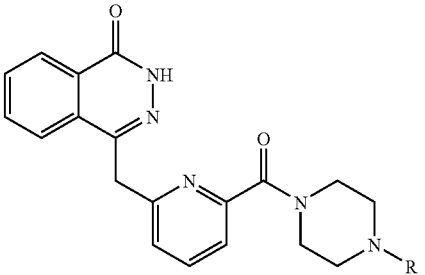 | 3.66 | 460 |

(b) The appropriate isocyanate (0.24 mmol) was added to a solution of 4-[4-(piperazine-1-carbonyl)-pyridin-2-ylmethyl]-2H-phthalazin-1-one (vb) in dichloromethane (2 ml). The reaction was stirred at room temperature for 16 hours. The reaction mixtures were then purified by preparative HPLC.

The compounds synthesised are set out below.

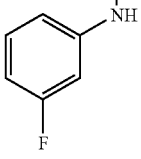

| Compound | R | Rt (min) | M + 1 |
|---|---|---|---|
| 13 | 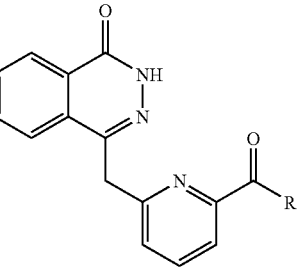 | 3.67 | 487 |

(c) A mixture of 6-(4-oxo-3,4-dihydro-phthalazin-1-ylmethyl)-pyridine-2-carboxylic acid (iva)(0.3 g, 1.1 mmol), triethylamine (0.3 ml, 2.1 mmol), the appropriate amine (1.3 mmol) and 2-(1H-benzotriazole-1-yl)-1,1,3,3-tetramethyluronium hexafluorophosphate (0.5 g, 1.3 mmol) in dimethylformamide (10 ml) was stirred for 18 hours. The reaction mixtures were then purified by preparative HPLC.

The compounds synthesised are set out below.

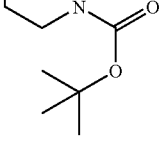

| Compound | R | Rt (min) | M + 1 |
|---|---|---|---|
| 14 | 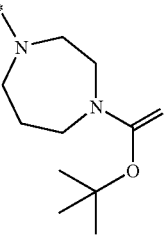 | 3.73 | 450 |
| 15 | 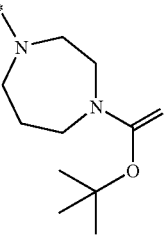 | 3.8 | 464 |

Example 3

(a) The appropriate acid chloride (0.24 mmol) was added to a solution of 4-[5-(piperazine-1-carbonyl)-furan-2-ylmethyl]-2H-phthalazin-1-one (vd) in dichloromethane (2 ml). Hunigs base (0.4 mmol) was then added and the reaction was stirred at room temperature for 16 hours. The reaction mixtures were then purified by preparative HPLC.

The compounds synthesised are set out below.

| Compound | R | Rt (min) | M + 1 |
|---|---|---|---|
| 16 | ethylsulfonyl | 4.23 | 431 |
| 17 | cyclopentylcarbonyl | 4.46 | 435 |
| 18 | mesitylsulfonyl | 5.42 | 521 |
| 19 | 3-fluorobenzoyl | 4.47 | 461 |
| 20 | cyclopropylcarbonyl | 4.49 | 407 |
| 21 | cyclohexylcarbonyl | 4.64 | 449 |
| 22 | propanoyl | 4.00 | 395 |

| Compound | R | Rt (min) | M + 1 |
|---|---|---|---|
| 23 | acetyl | 3.85 | 381 |

(b) The appropriate isocyanate (0.24 mmol) was added to a solution of 4-[5-(piperazine-1-carbonyl)-furan-2-ylmethyl]-2H-phthalazin-1-one (vd) in dichloromethane (2 ml). The reaction was stirred at room temperature for 16 hours. The reaction mixtures were then purified by preparative HPLC.

The compounds synthesised are set out below.

| Compound | R | Rt (min) | M + 1 |
|---|---|---|---|
| 24 | (3-fluorophenyl)aminocarbonyl | | |
| 25 | morpholinocarbonyl | | |

(c) A mixture of 5-(4-oxo-3,4-dihydro-phthalazin-1-ylmethyl)-furane-2-carboxylic acid (ivd) (1.1 mmol), triethylamine (0.3 ml, 2.1 mmol), the appropriate amine (1.3 mmol) and 2-(1H-benzotriazole-1-yl)-1,1,3,3-tetramethyluronium hexafluorophosphate (0.5 g, 1.3 mmol) in dimethylformamide (10 ml) was stirred for 18 hours. The reaction mixtures were then purified by preparative HPLC.

The compounds synthesised are set out below.

[Structure: 4-[(5-(piperazine-1-carbonyl)furan-2-yl)methyl]-2H-phthalazin-1-one with R on piperazine N]

| Compound | R | Rt (min) | M + 1 |
|---|---|---|---|
| 26 | cyclohexyl-CH2-* | 3.69 | 421 |
| 27 | 2-pyridyl-* | 3.61 | 416 |
| 28 | 4-acetylphenyl-* | 4.64 | 457 |
| 29 | 2-furoyl-* | 4.21 | 433 |
| 30 | 3-methoxyphenyl-* | 4.96 | 445 |
| 31 | cinnamyl-* (PhCH=CHCH2-) | 3.93 | 455 |
| 32 | 4-chlorobenzyl-* | 3.89 | 463 |
| 33 | 2-fluorophenyl-* | 5.09 | 433 |
| 34 | tetrahydrofuran-2-carbonyl-* | 3.99 | 437 |
| 35 | 2-pyrimidyl-* | 4.35 | 417 |
| 36 | 2-methoxyethyl-* | 3.51 | 397 |

[Structure: 4-[(5-(R-carbonyl)furan-2-yl)methyl]-2H-phthalazin-1-one]

| Compound | R | Rt (min) | M + 1 |
|---|---|---|---|
| 37 | 4-methyl-1,4-diazepan-1-yl-* | 3.42 | 367 |
| 38 | 4-morpholinopiperidin-1-yl-* | 3.51 | 423 |

Example 4

(a) The appropriate acid chloride (0.24 mmol) was added to a solution of 4-[5-(piperazine-1-carbonyl)-thiophen-2-ylmethyl]-2H-phthalazin-1-one (vc) in dichloromethane (2 ml). Hunigs base (0.4 mmol) was then added and the reaction was stirred at room temperature for 16 hours. The reaction mixtures were then purified by preparative HPLC.

The compounds synthesised are set out below.

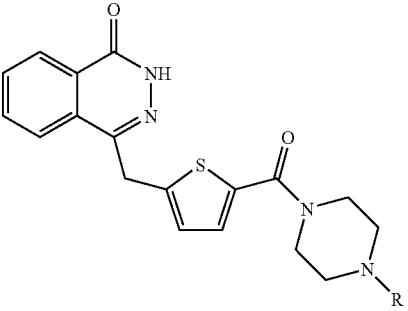

| Compound | R | Rt (min) | M + 1 |
|---|---|---|---|
| 39 | 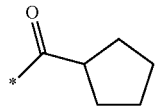 | 4.43 | 447 |
| 40 | 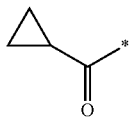 | 4.65 | 451 |
| 41 | 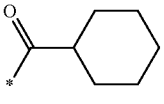 | 4.23 | 423 |
| 42 | 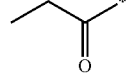 | 4.81 | 465 |
| 43 | 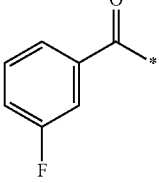 | 4.14 | 411 |
| 44 | 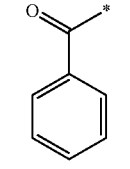 | 4.80 | 492 |
| 45 | 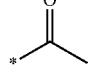 | 4.53 | 459 |
| 46 | 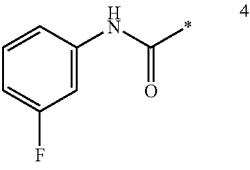 | 3.96 | 397 |

(b) The appropriate isocyanate (0.24 mmol) was added to a solution of 4-[5-(piperazine-1-carbonyl)-thiophen-2-ylmethyl]-2H-phthalazin-1-one (vc) in dichloromethane (2 ml). The reaction was stirred at room temperature for 16 hours. The reaction mixtures were then purified by preparative HPLC.

The compounds synthesised are set out below.

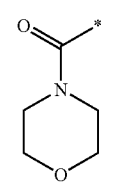

| Compound | R | Rt (min) | M + 1 |
|---|---|---|---|
| 47 | 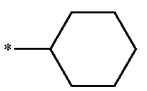 | 4.66 | 477 |
| 48 | 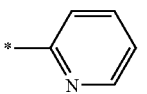 | 4.10 | 468 |

(c) A mixture of 5-(4-oxo-3,4-dihydro-phthalazin-1-ylmethyl)-thiophene-2-carboxylic acid (ivc)(1.1 mmol), triethylamine (0.3 ml, 2.1 mmol), the appropriate amine (1.3 mmol) and 2-(1H-benzotriazole-1-yl)-1,1,3,3-tetramethyluronium hexafluorophosphate (0.5 g, 1.3 mmol) in dimethylformamide (10 ml) was stirred for 18 hours. The reaction mixtures were then purified by preparative HPLC.

The compounds synthesised are set out below.

| Compound | R | Rt (min) | M + 1 |
|---|---|---|---|
| 49 | cyclohexyl | 3.85 | 437 |
| 50 | pyridyl | 3.73 | 432 |

-continued

| | | Rt (min) | M + 1 |
|---|---|---|---|
| 51 | *-C6H4-C(O)CH3 (para-acetylphenyl) | 4.87 | 473 |
| 52 | *-C6H4-OCH3 (meta-methoxyphenyl) | 5.21 | 461 |
| 53 | *-CH2-C6H4-Cl (para-chlorobenzyl) | 4.14 | 479 |
| 54 | *-C6H4-F (ortho-fluorophenyl) | 5.33 | 449 |

[Structure: 4-[(5-R-carbonyl-thiophen-2-yl)methyl]-2H-phthalazin-1-one]

| Compound | R | Rt (min) | M + 1 |
|---|---|---|---|
| 55 | N-methyl-1,4-diazepan-1-yl | 3.53 | 383 |

Example 5

(a) An appropriate acid chloride (0.13 mmol) was added to a solution of 4-[2-(piperazine-1-carbonyl)-pyridin-4-ylmethyl]-2H-phthalazin-1-one (ve)(0.045 g, 0.13 mmol) in anhydrous DCM (1.0 mL). N'N'-diisopropylethylamine (47 μL, 0.26 mmol) was then added and stirred at room temperature for 18 hours. The reaction mixtures were then purified by preparatory HPLC.

The compounds synthesised are set out below.

[Structure: 4-[2-(4-R-piperazine-1-carbonyl)-pyridin-4-ylmethyl]-2H-phthalazin-1-one]

| Compound | R | Rt (min) | M + 1 |
|---|---|---|---|
| 56 | cyclohexylcarbonyl | 4.12 | 460 |
| 57 | cyclopropylcarbonyl | 3.60 | 418 |
| 58 | cyclopentylcarbonyl | 3.97 | 446 |
| 59 | morpholine-4-carbonyl | 3.50 | 463 |
| 60 | 4-methyl-4H-1,2,3-thiadiazole-5-carbonyl | 3.71 | 476 |
| 61 | thiophene-2-carbonyl | 3.85 | 460 |
| 62 | benzoyl | 3.86 | 454 |

(b) To a solution of 4-(4-oxo-3,4-dihydro-phthalazin-1-ylmethyl)-pyridine-2-carboxylic acid (ive)(0.037 g, 0.13 mmol) in anhydrous dimethylacetamide (1 mL) was added appropriate secondary amine (0.14 mmol) and O-benzotriazole-N,N,N',N'-tetramethyl-uronium-hexafluoro-phosphate (0.060 g, 0.16 mmol). The mixture was stirred for 5 minutes before N'N'-diisopropylethylamine (0.47 μL, 0.26 mmol) was added and stirred at room temperature overnight. The reaction mixtures were then purified by preparatory HPLC.

The compounds synthesised are set out below.

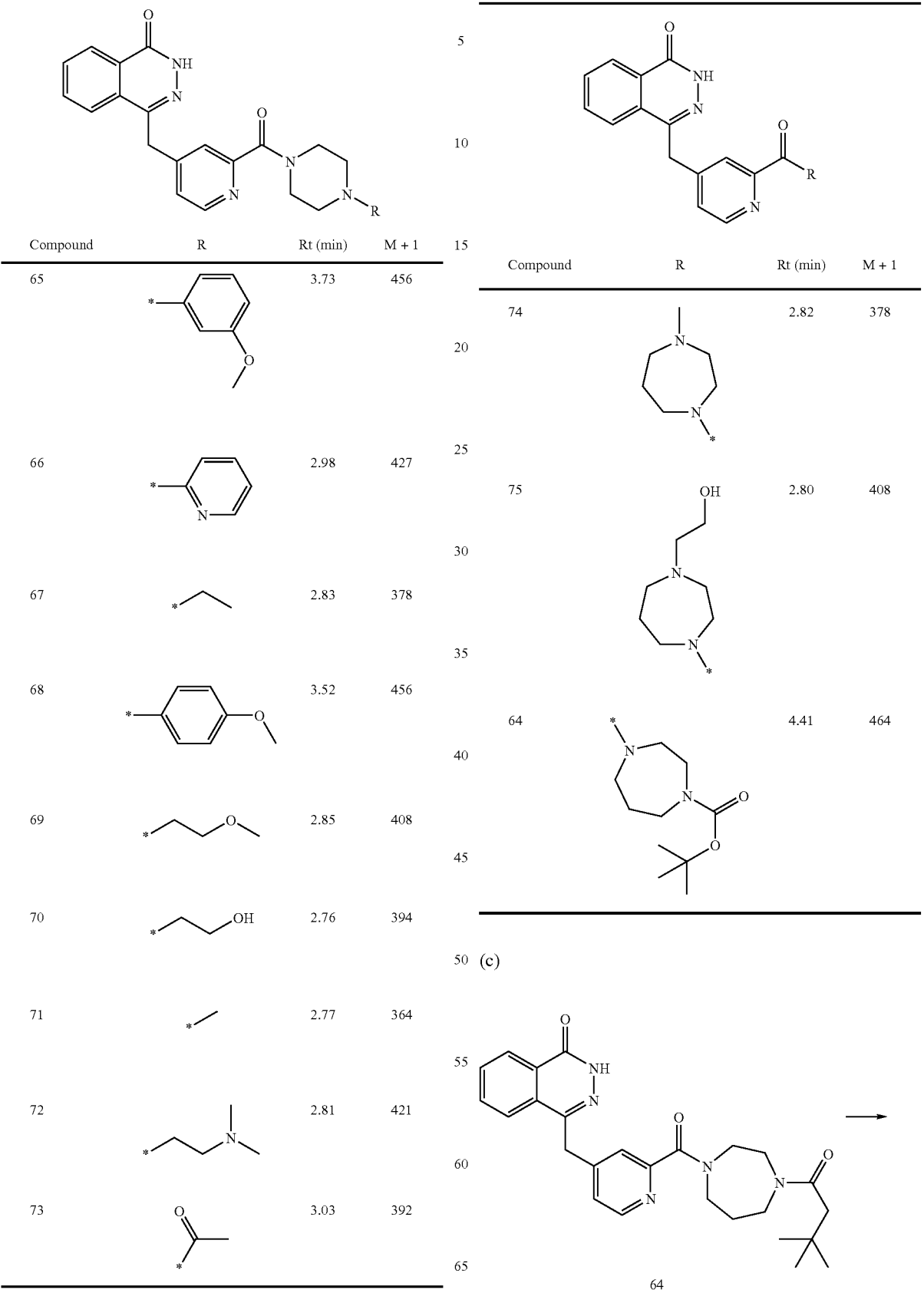

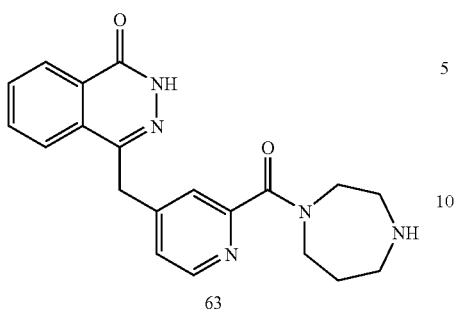

Compound 64 was deprotected using concentrated HCl in an organic solvent, to yield compound 63. Rt 3.21 mins, M+1 364.

Example 6

Alternative Synthesis of 5

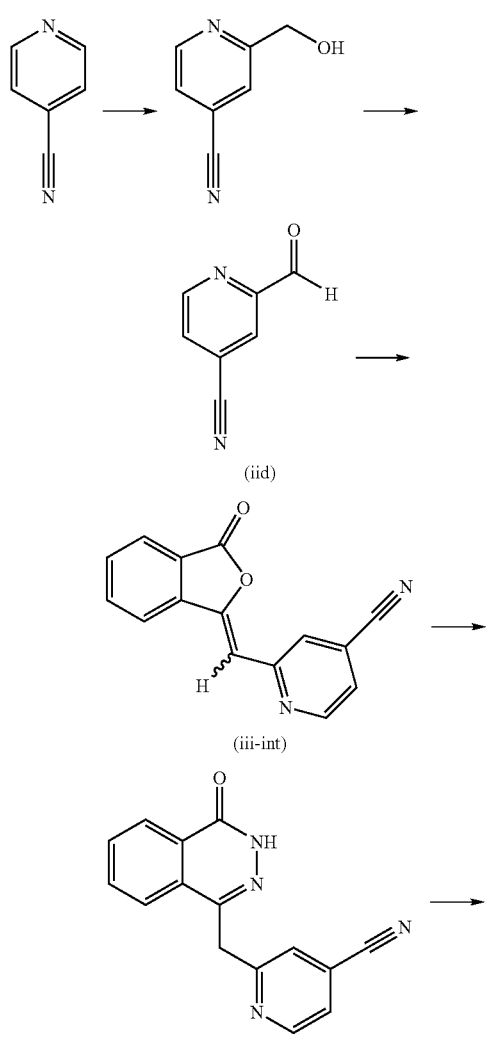

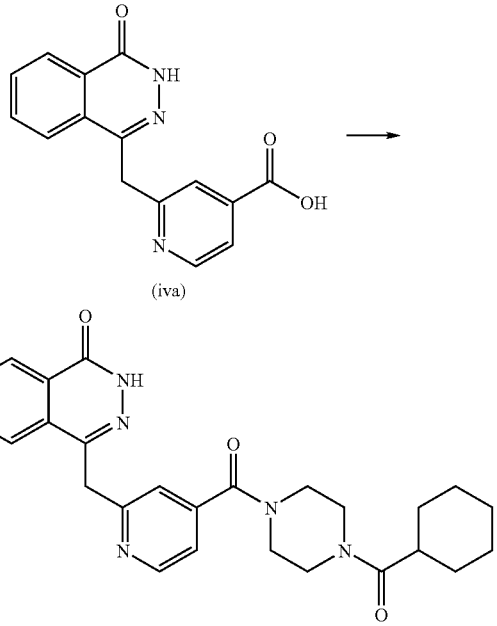

(a) 2-Hydroxymethyl-isonicotinonitrile

To a stirred solution of 4-cyanopyridine (10.4 g, 100.0 mmol) in methanol (100 mL) and water (50 mL) at room temperature was added conc sulfuric acid (5 mL), a slight exotherm was noted. After 10 minutes iron sulphate heptahydrate (910 mg, 3.0 mmol) was added and the reaction immediately turned a dark yellow/orange. After sonication of the reaction mixture under nitrogen for 20 minutes, hydroxylamine —O-sulfuric acid (11.3 g, 100.0 mmol) was added in one portion. A slight exotherm was noted after 10 minutes, the reaction was maintained under a nitrogen atmosphere.

After 2 hours additional hydroxylamine-O-sulfuric acid (11.3 g, 100.0 mmol) was added together with conc sulfuric acid (5 mL) and iron(II)sulphate heptahydrate (910 mg, 3.0 mmol). After a further 3 hours of stirring the reaction was neutralized by addition of sodium carbonate (18.0 g 200 mmol). The mixture was then diluted with water (100 ml) and filtered to remove a deep red/brown ppt, the filtrate was concentrated to dryness and the resulting solid dissolved in water (50 mL) and extracted with EtOAc (5×100 ml). The combined organics were dried over $MgSO_4$ and concentrated in vacuo to afford a 6.1 g of crude grey solid.

The material was then subjected to flash chromatography, eluent 8:1 Hex:EtOAc to remove the unreacted 4-cyanopyridine and then polarity increased to 2:1, Hex:EtOAc to isolated the desired product as a fluffy white solid (rf 0.5, 2:1 Hex/EtOAc). Single peak in LC-MS analysis, (3.3 g, 24.6%), m/z (LC-MS, ESP), RT=1.70 mins, (M+H)=135.0. $^1H$ NMR (300 MHz) 8.72 (1H, dd, J 0.9, 6.0 Hz), 7.78 (1H, m), 7.71 (1H, dt, J 0.9, 6.0 Hz), 5.65 (1H, t, J=6.9 Hz—OH), 4.61 (1H, d, J=6.9 Hz); $^{13}C$ NMR (100 MHz), 163.72, 149.85, 123.60, 121.69, 119.77, 116.99, 63.70;

(b) 2-Formyl-isonicotinonitrile (iid)

To a cooled solution of oxalyl chloride (13.2 mL, 150 mmol) in anhydrous DCM (86 mL) under nitrogen atmosphere at −78° C. was added DMSO (21.2 mL dropwise over 20 minutes. The mixture was stirred for 15 minutes at (−78° C.) before 2-hydroxymethyl-isonicotinonitrile (4.0 g, 30 mmol) dissolved in anhydrous DCM (60 mL) was added dropwise to the reaction mixture over 5 minutes. The reaction was stirred for 2 hrs at −78° C. maintaining a nitrogen atmosphere. A white solid precipitate formed and the temperature was raised to (−55° C.) and triethylamine (6.15 mL, 450 mmol) was added dropwise for over 15 minutes, cooling bath was removed allowing the mixture to warm to room temperature over 2 hrs. The mixture was diluted with DCM (400 mL) and washed with brine (2×50 mL). The aqueous phase was extracted with DCM (3×50 mL). The combined organic layers were combined and concentrated in vacuo. A buff white solid was isolated that was used without any further purification. Single peak in LC-MS analysis, (yield taken to be quantitative), m/z (LC-MS, ESP), RT=2.53 mins, (M+H)=133.0.

(c) 2-(3-Oxo-3H-isobenzofuran-1-ylidenemethyl)-isonicotinonitrile (iii-int)

To a cooled suspension (ca 0° C.) of [(3-Oxo-1,3-dihydro-isobenzofuran-1-yl)-phosphonic acid dimethyl ester]phosphonate (i)(8.0 g, 33.0 mmol) in THF (400 mL) was added crude 2-formyl-isonicotinonitrile (iid)(30.0 mmol) followed by triethylamine (6.2 mL, 33.0 mmol). The mixture was stirred for 30 minutes at 0° C. and then allowed to warm overnight.

The reaction mixture was then evaporated in vacuo, the resultant solid was then washed with ethyl acetate (2×50 mL), methanol (1×15 mL) and then diethyl ether (2×20 mL). Two peaks were detected in LC-MS analysis, the desired product; m/z (LC-MS, ESP), RT=4.27 mins, (M+H)=249.0, and an impurity peak (approx 40%)RT=4.47 mins M+H 194). This material used without need for any purification.

(d) 2-(4-Oxo-3,4-dihydro-phthalazin-1-ylmethyl)-isonicotinonitrile

To crude 2-(3-oxo-3H-isobenzofuran-1-ylidenemethyl)-isonicotinonitrile (iii-int)(approx 4.0 mmol) suspended in water (30 mL) and hydrazine monohydrate (2 mL). The reaction mixture was then heated to 90° C. for 90 minutes and then cooled to room temperature. The resulting suspension was filtered and washed with methanol (5 mL), water (10 ml) and then ethyl ether (2×30 mL). A buff solid was isolated with single peak in LC-MS analysis. (0.61 g, 26.7% over 3 steps); m/z (LC-MS, ESP), RT=3.48 mins, (M+H)=263.0.

(e) 2-(4-Oxo-3,4-dihydro-phthalazin-1-ylmethyl)-isonicotinic acid (iva)

To a suspension of 2-(4-oxo-3,4-dihydro-phthalazin-1-ylmethyl)-isonicotinonitrile (0.54 g, 2.06 mmol) in absolute ethanol (2.5 mL), was added conc hydrochloride acid (1.3 mL). The reaction mixture was then heated to 70° C. overnight. The reaction was then cooled to 5° C. and then the white suspension was t filtered and washed with water (2×5 mL), then diethyl ether (2×20 mL). A bright yellow solid was isolated with single peak in LC-MS analysis, (0.49 g, 88%); m/z (LC-MS, ESP), RT=3.08 mins, (M+H)=282; & (2M+H)=563.

(f) 4-[4-(4-Cyclohexanecarbonyl-piperazine-1-carbonyl)-pyridin-2-ylmethyl-2H-phthalazin-1-one (5)

To a stirred solution of 2-(4-oxo-3,4-dihydro-phthalazin-1-ylmethyl)-isonicotinic acid (iva)(0.25 g, 0.89 mol) in diemthylacetamide (2 mL) was added cyclohexyl-piperazin-1-yl-methanone (0.20 g, 1.0 mmol) followed by HBTU (0.38 g, 1.0 mmol) and diisopropyl ethyl amine (0.35 mL, 20.0 mmol) and stirred. The reaction mixture was then concentrated in vacuo and resulting oil subjected to flash chromatography eluent 9:1 EtOAc/MeOH. (rf of 0.3) The titled compound was isolated as a white solid. Single peak in LC-MS analysis, (0.18 g, 56%); m/z (LC-MS, ESP), RT=4.07 mins, (M+H)=460; $^1$H NMR (300 MHz) 12.57 (1H, S —NH), 8.56 (1H, d, J=5.1 Hz), 8.26 (1H, dd, J 1.5, 8.1 Hz), 7.95-7.80 (3H, m), 7.38 (1H, S), 7.25 (1H, d, J=5.7 Hz), 4.51 (2H, S), 3.56-3.17 (8H, m), 2.58 (1H, m), 1.71-1.61 (5H, m), 1.38-1.22 (5H, m).

Example 7

In order to assess the inhibitory action of the compounds, the following assay was used to determine $IC_{50}$ values (Dillon, et al., *JBS.*, 8(3), 347-352 (2003)).

Mammalian PARP, isolated from Hela cell nuclear extract, was incubated with Z-buffer (25 mM Hepes (Sigma); 12.5 mM $MgCl_2$ (Sigma); 50 mM KCl (Sigma); 1 mM DTT (Sigma); 10% Glycerol (Sigma) 0.001% NP-40 (Sigma); pH 7.4) in 96 well FlashPlates (TRADE MARK) (NEN, UK) and varying concentrations of said inhibitors added. All compounds were diluted in DMSO and gave final assay concentrations of between 10 and 0.01 μM, with the DMSO being at a final concentration of 1% per well. The total assay volume per well was 40 μl.

After 10 minutes incubation at 30° C. the reactions were initiated by the addition of a 10 μl reaction mixture, containing NAD (5 μM), $^3$H-NAD and 30mer double stranded DNA-oligos. Designated positive and negative reaction wells were done in combination with compound wells (unknowns) in order to calculate % enzyme activities. The plates were then shaken for 2 minutes and incubated at 30° C. for 45 minutes.

Following the incubation, the reactions were quenched by the addition of 50 μl 30% acetic acid to each well. The plates were then shaken for 1 hour at room temperature.

The plates were transferred to a TopCount NXT (TRADE MARK) (Packard, UK) for scintillation counting. Values recorded are counts per minute (cpm) following a 30 second counting of each well.

The % enzyme activity for each compound is then calculated using the following equation:

$$\% \text{ Inhibition} = 100 - \left(100 \times \frac{(\text{cpm of unknowns} - \text{mean negative cpm})}{(\text{mean positive cpm} - \text{mean negative cpm})}\right)$$

$IC_{50}$ values (the concentration at which 50% of the enzyme activity is inhibited) were calculated, which are determined over a range of different concentrations, normally from 10 μM down to 0.001 μM. Such $IC_{50}$ values are used as comparative values to identify increased compound potencies.

All compounds tested had a $IC_{50}$ of less than 1 μM.

The following compounds have an $IC_{50}$ of less than 0.1 μM: 1-7, 9-14, 17-18, 21, 24, 26-29, 35, 50-52, 56-75.

The Potentiation Factor ($PF_{50}$) for compounds is calculated as a ratio of the $IC_{50}$ of control cell growth divided by the $IC_{50}$ of cell growth+PARP inhibitor. Growth inhibition curves for both control and compound treated cells are in the presence of the alkylating agent methyl methanesulfonate (MMS). The test compounds were used at a fixed concentration of 0.2 micromolar. The concentrations of MMS were over a range from 0 to 10 μg/ml. Cell growth was assessed using the sulforhodamine B (SRB) assay (Skehan, P., et al., (1990) New calorimetric cytotoxicity assay for anticancer-drug screening. J. Natl. Cancer Inst. 82, 1107-1112.). 2,000 HeLa cells were seeded into each well of a flat-bottomed 96-well microtiter plate in a volume of 100 μl and incubated for 6 hours at 37° C. Cells were either replaced with media alone or with media containing PARP inhibitor at a final concentration of 0.5, 1 or 5 μM. Cells were allowed to grow for a further 1 hour before the addition of MMS at a range of concentrations (typically 0, 1, 2, 3, 5, 7 and 10 μg/ml) to either untreated cells or PARP inhibitor treated cells. Cells treated with PARP inhibitor alone were used to assess the growth inhibition by the PARP inhibitor.

Cells were left for a further 16 hours before replacing the media and allowing the cells to grow for a further 72 hours at 37° C. The media was then removed and the cells fixed with 100 μl of ice cold 10% (w/v) trichloroacetic acid. The plates were incubated at 4° C. for 20 minutes and then washed four times with water. Each well of cells was then stained with 100% of 0.4% (w/v) SRB in 1% acetic acid for 20 minutes before washing four times with 1% acetic acid. Plates were then dried for 2 hours at room temperature. The dye from the stained cells was solubilized by the addition of 100% of 10 mM Tris Base into each well. Plates were gently shaken and left at room temperature for 30 minutes before measuring the optical density at 564 nM on a Microquant microtiter plate reader.

All the compounds tested had a $PF_{50}$ at 200 nM of at least 1. The following compounds had a $PF_{50}$ at 200 nM of at least 2: 2, 3, 5, 6, 9, 10, 12, 13, 56, 57, 58, 62, 65, 66, 67, 74, 75.

The invention claimed is:
1. A compound of formula (I):

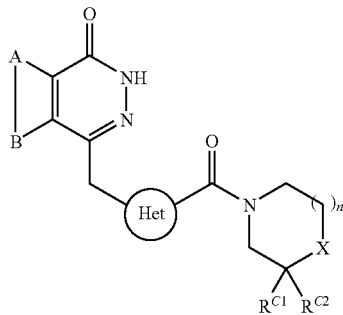

and isomers and salts thereof, wherein:
A and B together represent a fused benzene ring;
X is $NR^X$;
if $X=NR^X$ then n is 1;
$R^X$ is optionally substituted $C_{5-20}$ aryl;
$R^{C1}$ and $R^{C2}$ are both hydrogen; and
Het is selected from

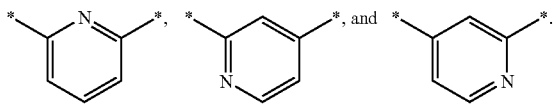

2. A pharmaceutical composition comprising a compound according to claim 1 and a pharmaceutically acceptable carrier or diluent.

3. A method of treatment of disease ameliorated by the inhibition of PARP, comprising administering to a subject in need of treatment a therapeutically-effective anount of compound according to claim 1, wherein the disease is selected from the group consisting of: septic shock; ischaemic injury; reperfusion injury; haemorraghic shock; and multiple sclerosis.

4. A compound according to claim 1, wherein Het is:

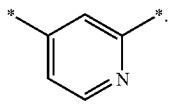

5. A compound according to claim 4, wherein $R^X$ is selected from:

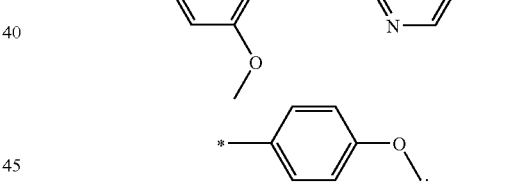

* * * * *

UNITED STATES PATENT AND TRADEMARK OFFICE
CERTIFICATE OF CORRECTION

PATENT NO. : 7,666,870 B2 Page 1 of 1
APPLICATION NO. : 12/143208
DATED : February 23, 2010
INVENTOR(S) : Muhammad Hashim Javaid et al.

It is certified that error appears in the above-identified patent and that said Letters Patent is hereby corrected as shown below:

Title Page
Column 1, (73) Assignee: insert --Kudos Pharmaceuticals Limited, Cambridge (GB)--

Signed and Sealed this

Thirteenth Day of July, 2010

David J. Kappos
*Director of the United States Patent and Trademark Office*